United States Patent [19]
Sato et al.

[11] Patent Number: 5,459,061
[45] Date of Patent: Oct. 17, 1995

[54] HYBRIDOMAS PRODUCING MONOCLONAL ANTIBODIES WHICH SPECIFICALLY BIND TO CONTINUOUS EPITOPE ON THE HUMAN EGF RECEPTOR AND COMPETE WITH EGF FOR BINDING TO THE EGF RECEPTOR

[75] Inventors: J. Denry Sato; Dianging Wu, both of Lake Placid, N.Y.; Lihua Wang, Shanghai, China

[73] Assignee: W. Alton Jones Cell Science Center, Inc., Lake Placid, N.Y.

[21] Appl. No.: 133,274

[22] Filed: Oct. 7, 1993

Related U.S. Application Data

[63] Continuation of Ser. No. 470,642, Jan. 26, 1990, abandoned.
[51] Int. Cl.$^6$ ............................. C12N 5/20; C07K 16/28; C07K 16/30
[52] U.S. Cl. .................. 435/240.27; 530/388.22; 530/388.8; 435/172.2; 435/70.21
[58] Field of Search ............................ 530/388.22, 388.8; 435/240.27, 172.2, 70.21

OTHER PUBLICATIONS

Mendelsohn et al. Cellular & Mol. Biol. of Tumors & Pot'l. Clin. Applications pp. 307–312. 1988.
Kudlow et al. J Biol. Chem. 259:11895–11900, 1984.
Parsons–Chandler et al. J Biol Chem 260:3360–3367, 1987.
Wu et al. J. Biol. Chem. 264:17469–17454 15 Oct. 1989.
Lerner, Nature 299:592 1982.
Ullrich et al. Nature 309:418 1984.
Appel et al. J. Immunology 144:976–983, 1990.
Dayhoff et al. "Atlas of Protein Sequence and Structure" vol. 5:89–99, 1972.

*Primary Examiner*—Paula K. Hutzell
*Attorney, Agent, or Firm*—Browdy and Neimark

[57] ABSTRACT

Hybridomas producing monoclonal antibodies that specifically bind to the human EGF receptor and compete with EGF for binding to the EGF receptor are described. The subject monoclonal antibodies bind to an epitope located between residues Ala-351 and Asp-364 of the EGF receptor, which is not denatured by boiling, treatment with detergent or treatment with a reducing agent.

7 Claims, 13 Drawing Sheets

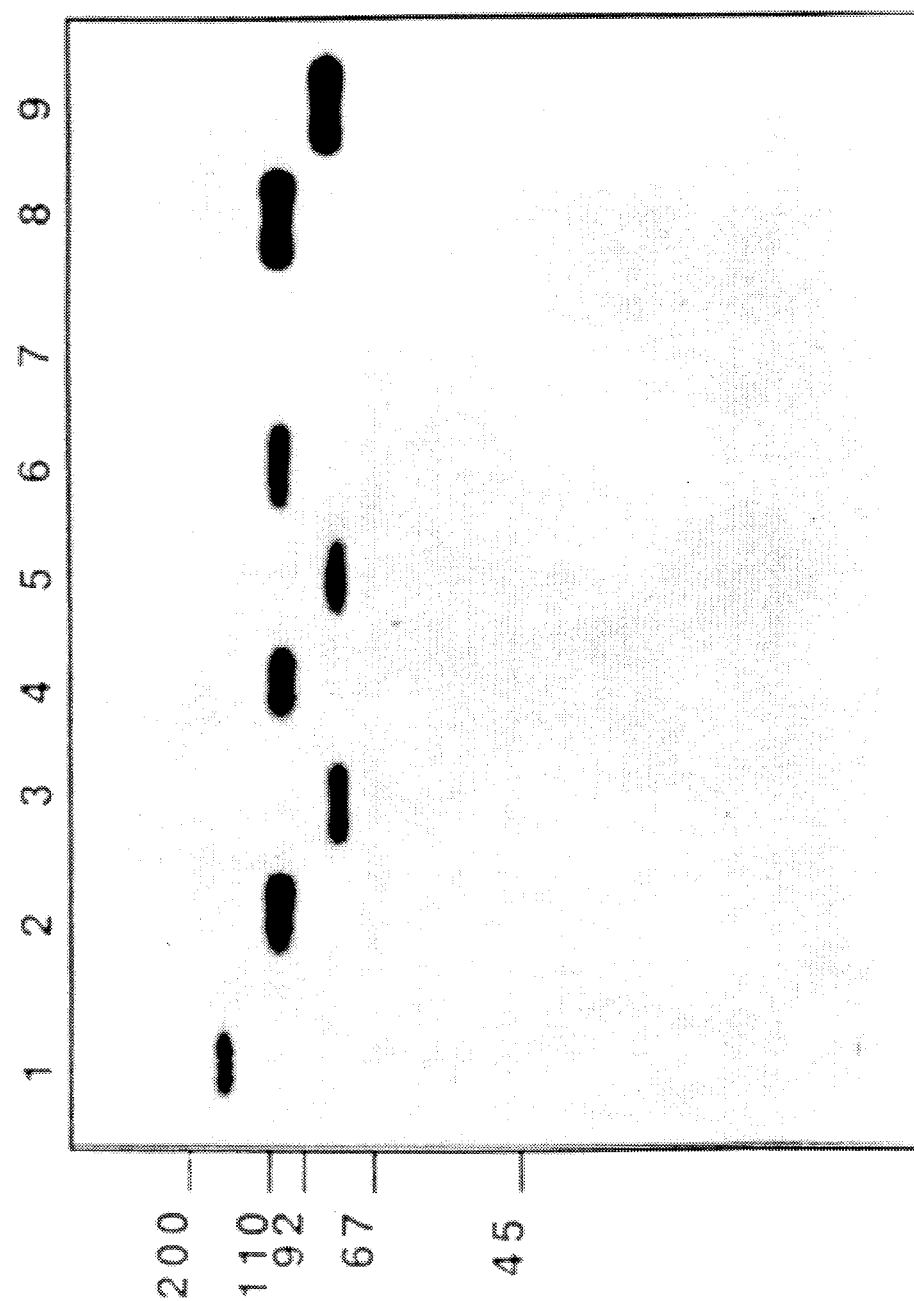

```
                          295     300
                          Glu Glu Asp Gly Val Arg Lys Cys Lys Lys Cys Glu Gly Pro Cys Arg
                                              Asn                     Asp      Leu     Ser
                                                                                           330
Lys Val Cys Asn Gly  Ile Gly  Ile Gly Glu Phe Lys Asp Ser Leu Ser  Ile Asn Ala Thr
                                          Leu     Gly Ile
                                      340
Asn  Ile Lys His Phe Lys Asn Cys Thr Ser Ile Ser Gly Asp Leu His  Ile Leu Pro Val
                    Asp Ser               Lys           Asn           Val Ser
                                                     360                               370
                          Ala Phe Arg Gly Asp Ser Phe Thr His Thr Pro Leu Asp Pro Gln Glu Leu Asp  Ile
                                       Leu                    Ala               Lys            Leu    Lys Lys    Val
```

HYBRIDOMAS PRODUCING MONOCLONAL ANTIBODIES WHICH SPECIFICALLY BIND TO CONTINUOUS EPITOPE ON THE HUMAN EGF RECEPTOR AND COMPETE WITH EGF FOR BINDING TO THE EGF RECEPTOR

This invention was made with Government support under NIH grant No. PO1 CA37589-07 awarded by the National Cancer Institute. The Government has certain rights in the invention. This application is a continuation of application Ser. No. 07/470,64, filed Jan. 26, 1990, now abandoned.

SUMMARY OF THE INVENTION

The control of human cell growth is of medical importance. As a result, growth factors, such as epidermal growth factor (EGF), are of interest, as cell growth is regulated by the interaction between growth factors and their receptors in the cell. Here, we disclose the invention of monoclonal antibodies that are useful because they block the interaction of EGF with human cell receptors and inhibit cell growth. They are also useful because they are analytical reagents of great specificity. Also disclosed are segments of the EGF receptor of value as monoclonal antibody targets and immunogens or immunogen components.

The monoclonal antibodies we discovered are unusual anti-EGF receptor antibodies in that they also recognize deglycosylated and denatured EGF receptors. These properties were essential for us to determine the amino acid sequence of the epitope where the antibodies bind. Taking advantage of these properties and using cyanogen bromide fragments of a truncated form of the EGF receptor secreted by A431 cells (26) and synthetic peptides, we determined that all three antibodies recognize epitopes encompassed by 14 amino acids of the EGF receptor. This region of the receptor is located between the extracellular cysteine-rich domains and includes an Arg-Gly-Asp-Ser recognition sequence for cell adhesion receptors (27).

In additional experiments we allowed a truncated form of the human EGF receptor to bind to mouse EGF and then crosslinked the two entities with an amine-reactive crosslinking reagent, disuccinimidyl succinate (DSS). (Mouse EGF, a commonly used substitute for human EGF, was the form of EGF used in all experiments in this application.) This allowed us to pinpoint a single amino acid in the receptor that was linked to the EGF, indicating that the amino acid was in the EGF binding site. Combining the knowledge of the locations of that amino acid with the knowledge of the locations of the three antibody epitopes, as well as other information on the structure of the receptor, allowed us to the identify regions of the receptor of particular value as monoclonal antibody targets.

The EGF receptor

Among the known growth factors and receptors (1), intra-cellular signal transduction initiated by interactions between epidermal growth factor (EGF) and its receptor has been particularly well studied (2–5). EGF is a 53-residue polypeptide that stimulates the growth of a variety of cell types and is synthesized in the form of an $M_r$ 128,000 precursor molecule. The mature EGF receptor is an $M_r$ 170,000 glycoprotein with intrinsic tyrosine-specific protein kinase activity and contains two functional domains linked by a transmembrane region (11–14). The extracellular domain is heavily glycosylated and possesses a single EGF-binding site, and the intracellular portion of the receptor includes a tyrosine protein kinase domain with three COOH-terminal autophosphorylation sites at residues 1068, 1148, and 1173 (14–19). The extracellular domain of the EGF receptor contains a large number of cysteine residues, 51 in total, which are clustered in two regions (14). These cysteine residues are conserved in the extracellular domain of the chicken EGF receptor which is 75% identical to that of the human receptor (20). Similar clusters of cysteine residues have been found in the extra-cellular portions of the receptors for insulin, insulin-like growth factor I, nerve growth factor, and low density lipoprotein (2). Although these cysteine-rich regions probably contribute to receptor tertiary structure through the formation of intramolecular disulfide bridges, the role of these regions in receptor function has not been elucidated.

Very little is known about the structural features of the EGF receptor that are involved in the binding of EGF. Carpenter and Cohen observed that several lectins reversibly inhibited the binding of radiolabeled EGF to human fibroblasts (21). However, the antigenic specificities of monoclonal antibodies to EGF receptors of A431 human epidermoid carcinoma cells indicate that antibodies which block EGF binding do not recognize carbohydrate determinants while those with carbohydrate specificities do not inhibit EGF binding (22, 23). These results suggest that N-linked oligosaccharides, which comprise 40% of the mass of the EGF receptor extra-cellular domain (2) are not directly involved in EGF binding. In addition, Slieker et al. found that oligosaccharide addition to pro-EGF receptors was necessary to acquire the ability to bind EGF but that deglycosylated receptors retained binding activity (24). Lax et al. have cleaved with cyanogen bromide human EGF receptors cross-linked to $^{125}$I-EGF and have identified with anti-peptide antibodies a labeled $M_r$ 50,000 receptor fragment spanning residues 294–543, which is largely located between the two cysteine-rich regions of the extra-cellular domain (25). Thus, the EGF-binding site of the receptor resides within a 250-residue region of the extra-cellular domain. The location of the EGF binding site was not characterized in further detail.

BRIEF DESCRIPTION OF THE DRAWINGS

FIG. 2. Immunoreactivity of intact ERRP and deglycosylated ERRP. Full length A431 EGF receptor (lane 1), ERRP (lanes 2, 4, 6, and 8) and ERRP treated with endoglycosidase F (lanes 3, 5, 7, and 9) were electrophoresed in a 10% polyacrylamide gel under denaturing conditions and electrophoretically transferred to nitrocellulose. The membrane was reacted with monoclonal anti-bodies LA90 (lanes 1–3), LA58 (lanes 4 and 5), 455 IgG (lanes 6 and 7), and LA22 (lanes 8 and 9). Bound antibody was detected with $^{125}$I-protein A and autoradiography.

FIG. 3. Reverse phase HPLC chromatography of ERRP fragments after CNBr cleavage.

DETAILED DESCRIPTION OF PREFERRED EMBODIMENTS

Figure 1:
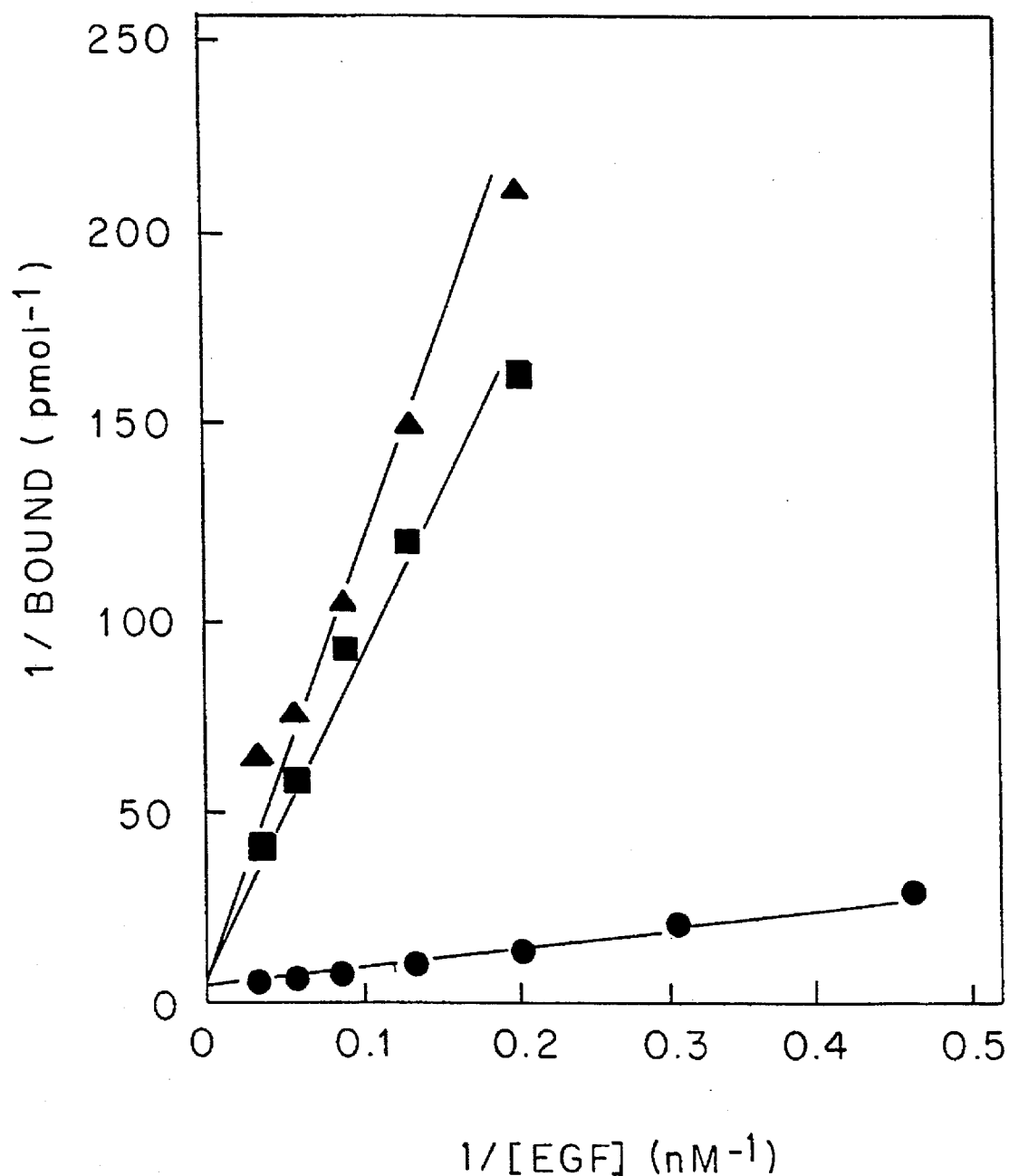
FIG. 1. Effect of monoclonal antibodies on $^{125}$I-EGF binding to A431 cells. Duplicate cultures of live A431 cells were incubated at 4° C. with increasing concentrations of 125I-EGF in the absence (filled in circles) or presence of 20 nM LA22 IgG (filled in triangles) or 20 nM LA58 IgG (filled in squares) as described under "Experimental Procedures." The data are shown in a double reciprocal Lineweaver-Burk plot.

The invention is, in its first aspect, a monoclonal antibody that competes with EGF binding to the natural human EGF receptor and binds to an epitope residing on the human EGF receptor between residues Cys-313 and Cys-446, which epitope remains immunologically active after denaturation. For the purpose of the present specification and claims, "denaturation" means an alteration of the three-dimensional conformation from that naturally occurring, including deglycosylation and reduction of disulfide bonds, such as, for example, by boiling, treatment with SDS or other strong detergent, and/or treatment with reducing agents, such as β-mercaptoethanol. Of course, "denaturation" as used herein does not comprehend conditions so extreme as to cause splitting of the peptide bonds or destruction of the amino acids. Cys-313 and Cys-446 are two residues that mark the limits of two cysteine-rich regions and also encompass the receptor segment that contains both the newly discovered antigenic determinant extending from residue Ala-351 to Asp-364 and the residue which can be cross-linked to bound EGF, Lys-336; any monoclonal antibody with the foregoing properties is considered part of the invention. In preferred embodiments the invention is either (1) a monoclonal antibody that reacts with an epitope residing on the receptor between residues Cys-313 and Asp-364, (2) one that reacts with an epitope between residues Lys-336 and Asp-364, (3) one that reacts with an epitope residing between residues Ala-351 and Asp-364, (4) one that reacts with the same epitope as a monoclonal antibody produced by a hybridoma selected from the group hybridoma ATCC HB 10342, hybridoma ATCC HB 10343, and hybridoma ATCC HB 10344, or (5) one that is produced by one of those three hybridomas.

In a second aspect, the invention is a chemical compound which includes an amino acid sequence comprising all or part of the human EGF receptor segment that extends from residue Phe-321 to residue Glu-367, said segment being substantially free of the remainder of the receptor. The receptor has a length effective to raise antibodies that compete with EGF binding. Usually, the minimum amino acid length to provide such immunogenicity is about ten amino acids. In preferred embodiments, the chemical compound includes all or part of that portion of the receptor segment that extends from (1) residue Lys-336 to residue Asp-364, or (2) residue Ala-351 to residue Asp-364, in each preferred embodiment said portion or part thereof being substantially free of the remainder of the receptor and other components of human cells. The segment may be one isolated from human cells by techniques which may or may not cause denaturation of the segment. It may also be one synthesized by known techniques. For those epitopes which bind to antibodies in both the natural or denatured form of the segment bearing the epitopes, a linear synthesized segment will also generate the desired antibodies, regardless of its natural conformation or glycosylation. Of course, the synthetic sequence may comprise segments which contain glycosylated structures or are otherwise manipulated in the laboratory to emulate the natural conformation and structure of the receptor.

The amino acid sequence present in the chemical compound of the present invention is a shortened segment of the entire human EGF receptor and as such does not comprehend the entire native receptor. However, the compound may contain other moieties or sequences for specified purposes, such as, for example, a carrier protein to enhance the immunogenicity of the compound.

Receptor fragments of the present invention may also be produced by recombinant DNA procedures. The DNA encoding the receptor fragment may be synthetic DNA, isolated genomic DNA, cDNA, or a combination thereof. The DNA can then be inserted into any appropriate vector, such as a plasmid or virus, and introduced into an appropriate host cell, either prokaryotic or eukaryotic. Such techniques are set forth, for example, in Sambrook et al, "Molecular Cloning: A Laboratory Manual", Second Edition, Cold Spring Harbor Laboratory Press, 1989. The present invention also comprehends such DNA, vectors and host cells.

In a further aspect, the invention is a process of inhibiting the growth of human cells which are EGF-responsive, which comprises allowing such cells to come into contact with a monoclonal antibody of the present invention.

In another aspect, the invention is the use of compounds including EGF sequences of the present invention in the known procedures of obtaining polyclonal or monoclonal antibodies by subjecting an animal to an immunogen and obtaining the antibodies, or the cells which produce the antibodies, raised in such animals. The cells may be used to form monoclonal hybridoma cell lines which produce a monoclonal antibody of the present invention.

In yet a further aspect, the present invention is a hybridoma capable of producing a monoclonal antibody in accordance with the present invention, and preferably one of hybridoma ATCC HB 10342, hybridoma ATCC HB 10343, and hybridoma ATCC HB 10344.

With respect to receptor segments, the segment between residues 321 and 367 is disclosed in this application. The residues from 321 to 336 can be split off with Lys-C endoproteinase. The linkage between residues 364 and 365 is acid labile; that property can be used to split off residues 365 to 367. The 14mer between residues 351 and 364 can be synthesized as described in this application. These methods, in combination with other methods described here, allow the production of a segment substantially free of the remainder of the receptor and other components of human cells as indicated by chromatographic and/or electrophoretic analysis.

MATERIALS AND METHODS

Abbreviations: EGF, epidermal growth factor; ERRP, EGF receptor-related protein; HPLC, high performance liquid chromatography; SDS, sodium dodecyl sulfate; DME, Dulbecco's Modified Eagle's medium; BSA, bovine serum albumin; ELISA, enzyme-linked immunosorbant assay.

Production of hybridomas and monoclonal antibodies, Hybridomas were produced by fusing X63-Ag8,653 mouse myeloma cells (30), obtained from the American Type Culture Collection (Rockville, MD), with splenocytes from Balb/c mice immunized with A431 human epidermoid carcinoma cells (22) as described previously (31,32). The hybridomas were selected in HAT-supplemented RD+5F (factor) medium (33) containing 5% fetal calf serum (FCS; Hyclone, Logan, UT), and they were subsequently cloned and maintained in RD+5F medium. The monoclonal antibodies LA22 IgG2a, LA58 lgG1, and LA90 IgG2a were selected for their ability to inhibit the binding of [$^{125}$I]EGF (receptor grade; Collaborative Research, Bedford, MA) to intact A431 cells (L. Wang and J. D. Sato, unpublished results) as described previously (31,34). Monoclonal antibodies were purified from serum-free hybridoma media by chromatography on protein A-Sepharose (Pharmacia Inc., Piscataway, N.J.) (35). Purified antibodies were dialyzed against phosphate-buffered saline and filter-sterilized.

Monoclonal antibody LA22 IgG2a, also referred to here as monoclonal antibody LA22, was deposited on Jan. 24, 1990, at the American Type Culture Collection, Rockville, Md. 20852, and was given the ATCC accession number HB 10342. Monoclonal antibody LA58 IgG1, also referred to here as monoclonal antibody LA58, was deposited on Jan. 24, 1990, at the American Type Culture Collection, Rockville, Md. 20852, and was given the ATCC accession number HB 10343. Monoclonal antibody LA90 IgG2a, also referred to here as monoclonal antibody LA90, was deposited on Jan. 24, 1990, at the American Type Culture Collection, Rockville, Md. 20852, and was given the ATCC accession number HB 10344.

Purification of EGF receptor-related protein (ERRP) from conditioned medium. The truncated form of the EGF receptor (ERRP; 26) secreted by A431 cells was purified from unsupplemented DME/F12 medium (Gibco, Grand Island, N.Y.) conditioned by A431 cells in roller bottle cultures. The conditioned medium was passed over a column of 528IGG EGF receptor monoclonal antibody (31, 34) immobilized on Affi-gel 10 (BioRad, Richmond, Calif.). Bound ERRP was eluted from the column in 0.1M citrate buffer (pH 4.0), and the eluate was dialyzed against distilled water and lyophilized.

Binding assays with EGF and monoclonal antibodies. The binding assays with EGF and monoclonal antibodies were done with paraformaldehyde-fixed A431 cells in punctured microtiter wells containing glass fiber filters (V and P Enterprises, San Diego, Calif.). EGF, LA22 IgG, LA58 IgG and LA90 IgG were labeled with Na[$^{125}$I] (Amersham, Arlington Heights, Ill.) by the chloramine T method. $2\times10^4$ A431 cells were incubated in duplicate wells with 0.3–0.5 nM $^{125}$I-ligand and increasing concentrations of unlabeled competing ligand in 50 µl DME/F12 medium containing 0.2% BSA. After two hours at room temperature the cells were washed four times with PBS containing 0.25% gelatin and 5% newborn calf serum. Cell-bound radioactivity was measured with a model 1274 LKB gamma counter. Maximum inhibition of binding was measured in the presence of a 200-fold excess of unlabeled homologous ligand.

The competitive nature of the antibody-mediated inhibition of $^{125}$I[EGF]-receptor binding was determined with confluent microtiter cultures of live A431 cells. Cells in duplicate cultures were incubated with increasing concentrations of [$^{125}$I]EGF (2.0×10$^5$ cpm/ng) in the presence or absence of 20 nM monoclonal antibody in DME/F12 medium containing 0.5% BSA. After two hours at 4° C. the cells were washed three times with 0.5% BSA in DME/F12 medium and were solubilized in 0.1N NaOH. Cell-bound radioactivity was corrected for non-specific binding in the presence of a 200-fold excess of unlabeled EGF. The results were analyzed in a double-reciprocal Lineweaver-Burk plot.

Immunodetection methods with purified monoclonal antibodies. For Western blotting (36) 2 μg each of intact A431 EGF receptors, ERRP, ERRP deglycosylated with endoglycosidase F containing peptide N-glycosidase (Boehringer-Mannheim, Indianapolis, IN) or ERRP peptides were electrophoresed in an SDS-polyacrylamide gel (SDS-PAGE) (37) using a miniprotean II apparatus (BioRad). Molecular weight markers were purchased from BioRad. The proteins were electrophoretically transferred with a mini-transblot assembly (BioRad) to 0.45 μm or 0.2 μm nitrocellulose (Schleicher and Schuell, Kenne, NH) in 25 nM Tris buffer (pH 8.3) containing 192 mM glycine and 20% (v/v) methanol. The nitrocellulose membranes were incubated with a 5% solution of non-fat dry milk for 1 hr and rinsed twice with TBS (20 nM Tris/500 nM NaCl/pH 7.5) to block non-specific binding sites. The nitrocellulose-bound proteins were incubated overnight at 4° C. with purified monoclonal antibodies at 1 μg/ml in a 1% solution of fraction V BSA (Sigma Chemical Co., St. Louis, Mo.). The membranes were rinsed with TBS and incubated for 1 hr in a 1:1000 dilution of affinity purified rabbit anti-mouse Ig (Cappel, Malvern, Pa.) in TBS. After two washes in TBS the nitrocellulose membranes were incubated for 1 hr in a 1:1000 dilution of $^{125}$I- protein A (50–100 μCi/μg; New England Nuclear, Boston, Mass.) in TBS. TBS-washed and air-dried membranes were exposed to XAR5 film (Kodak, Rochester, N.Y.) and bound antibody was detected by autoradiography. For dot-blotting peptides and protein were adsorbed to 0.2 μm nitrocellulose membranes (Schleicher and Schuell) in a 96-well dot-blot apparatus (BioRad), and the membranes were reacted with purified monoclonal antibodies and processed as described above.

Selective fragmentation of ERRP and peptide purification. Affinity-purified ERRP was reduced with 100 mM dithiothreitol (Sigma Chemical Co.) and carboxymethylated with iodoacetic acid (Sigma Chemical Co.). Alkylated ERRP was dialyzed against 70% formic acid (Aldrich Chemical Co., Milwaukee, Wis.) and was cleaved with cyanogen bromide (CNBr; Aldrich Chem. Co.) in the dark at 20° C. for 20 hr. Acid-sensitive aspartyl-prolyl peptide bonds (38,39) were cleaved at 100° C. for 30 min at 0.1% trifluoracetic acid (Pierce Chemical Co., Rockford, Ill.) as described by Tarr (28). For cleavage at glutamic acid residues CNBr-fragments of ERRP were digested with *S. aureus* V8 protease (Boehringer-Mannheim) at a 10:1 (w/w) ratio in 1% ammonium bicarbonate, pH 8, at 37° C. for 24 hr. ERRP was deglycosylated with endoglycosidase F (Boehringer-Mannheim) (6 mU/μg ERRP) for 12 hr at 37° C. in 50 μl 20 mM potassium phosphate (pH 7.0) containing 25 mM EDTA and 0.1% SDS. ERRP peptides were purified by reverse phase HPLC on Vydac columns (The Separations Group, Hesperia, Calif.) in aqueous solvents of 0.1% trifluoracetic acid (Pierce Chemical Co.) and acetonitrile (Burdick and Jackson, Muskegon, MI) using a Beckman model 344 HPLC gradient system (Beckman Instruments, Inc., San Ramon, Calif.).

Competitive binding assays using synthetic peptides. 96-well ELISA plates (Falcon, Oxnard, Calif.) were incubated overnight at 4° C. with 1 μg/ml purified ERRP in 50 mM ammonium bicarbonate, pH 9.6. Non-specific binding sites were blocked with 5% non-fat dry milk for 1 hr, and the plates were washed twice with 1% fraction V BSA (Sigma Chemical Co.) in 20 mM Tris buffer, pH 8.0 (EIA buffer). Purified monoclonal antibodies at 10 nM in EIA buffer were incubated with increasing concentrations of synthetic 24-residue or 14-residue ERRP peptides (see EXAMPLES) or purified ERRP for 1 hr at 20° C. The plates were washed three times with EIA buffer, and rabbit and anti-mouse IgG antibodies (1:1000 dilution in EIA buffer; Cappel) were added. After 1 hr the plates were washed with EIA buffer and $^{125}$I-protein A (New England Nuclear) in EIA buffer was added for a further hr. After a final series of washes, the plates were air-dried, and the wells were counted with a model 1274 LKB gamma counter.

Amino acid analysis, Edman degradation, and peptide synthesis. Phenylthiocarbamyl amino acid analysis and microsequence analysis were done using a model 420A PTC amino acid analyzer and a model 470 gas phase sequencer (both from Applied Biosystems, Inc.), respectively, as described by Crabb et al. (40). All sequencer reagents and solvents were from Applied Biosystems. With Beta-lactoglobulin A as a test substrate the sequencer gave initial yields of 40% and repetitive yields in excess of 92%. The N-terminal sequences of ERRP fragments were localized by comparison with the primary receptor structure deduced from cloned cDNA (14). Solid phase peptide synthesis was carried out essentially as described by Merrifield (41) using an Applied Biosystems Model 430A automatic peptide synthesizer. A 24 residue peptide (DLHILPVAFRGDSFTHTP-PLDPQD), a 14 residue peptide (AFRGDSFTHTPPLD), and a 4 residue peptide (RGDS) were synthesized using t-butyloxycarbonyl (tBOC-Na$^{alpha}$-protected amino acids and "Pam" resins (Applied Biosystems). Side chain protecting groups used were Asp(O Bzl), Ser(Bzl), Thr(Bzl), Arg-(Na$^{alpha}$Tos) and His(Bom) where Bzl=benzyl, Tos=toluene sulfoxyl, and Bom=benzyloxymethyl. The remaining amino acids had no side chain protecting groups. All amino acids were obtained from Peninsula Laboratories except tBoc-His(Bom), which was from Bachem. After assembly the protecting groups were removed and the peptide-resin anchoring bond was cleaved with 80–90% (v/v) anhydrous hydrogen fluoride in the presence of anisole and dimethylsulfide. Before use synthetic peptides were purified by reverse phase HPLC and were subjected to amino acid analysis and Edman degradation.

TABLE I

| | Amino Acid Analysis | | |
|---|---|---|---|
| | Peptide E[a] | | ERRP[b] |
| | Analysis 1 | Analysis 2 | (Residues 321–367) |
| Asx | 6.7 | 6.5 | 7 |
| Glx | 2.1 | 2.5 | 2 |
| Ser | 4.3 | 4.7 | 5 |
| Gly | 2.4 | 3.2 | 2 |

TABLE I-continued

Amino Acid Analysis

| | Peptide E[a] | | ERRP[b] |
| --- | --- | --- | --- |
| | Analysis 1 | Analysis 2 | (Residues 321–367) |
| His | 3.1 | 3.4 | 3 |
| Arg | 1.0 | 1.1 | 1 |
| Thr | 3.9 | 3.7 | 4 |
| Ala | 2.1 | 2.3 | 2 |
| Pro | 3.8 | 3.6 | 4 |
| Met | 0 | 0 | 0 |
| Tyr | 0 | 0 | 0 |
| Val | 1.0 | 1.1 | 1 |
| Ile | 3.8 | 3.5 | 4 |
| Leu | 4.1 | 3.8 | 4 |
| Phe | 4.0 | 3.4 | 4 |
| Lys | 3.2 | 3.0 | 3 |
| Total Residues | 46 | 46 | 46 |

Figure 8:
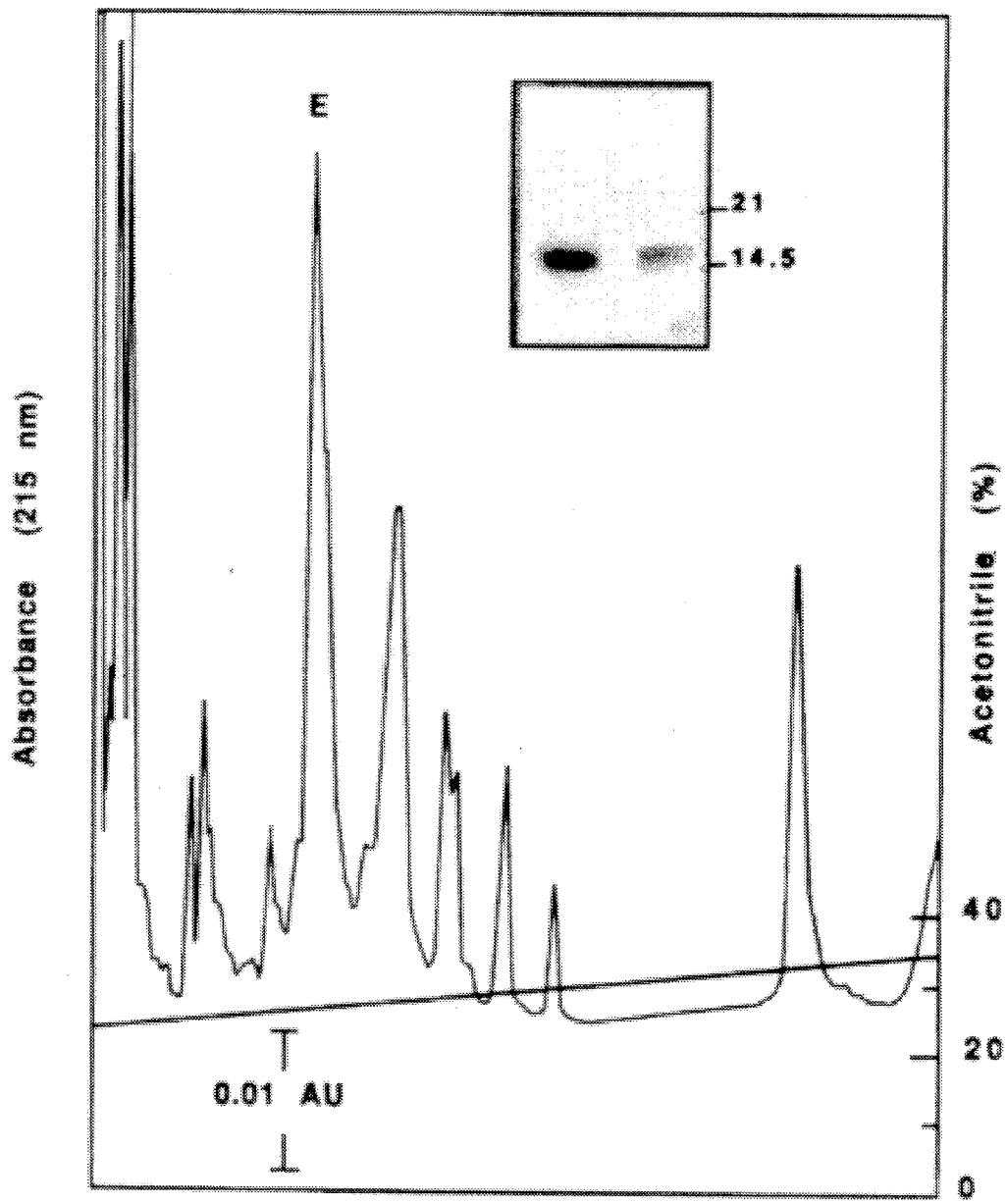
FIG. 8. S. aureus V8 protease digestion of LA22-reactive $M_r$ 43,000 and M 37,000 ERRP fragments. The $M_r$ 43,000 and $M_r$ CNBr- generated ERRP fragments (FIG. 4) were digested with S. aureus V8 protease at pH 8.0 (29), and the digestion products were chromatographed in a C-4 reverse phase HPLC column. Peak E, which reacted with L22 antibodies in a dot blot assay, was analyzed by N-terminal sequencing and electrophoresis. Edman degradation yielded a single sequence of FKDSLSIXATNIKHFKXCTSI. By SDS-PAGE, peak I was resolved into a single silver-stained band of $M_r$ 15,000 (inset, right lane) that reacted with LA22 antibodies (inset, left lane).

[a]Numbers of amino acid residues were calculated assuming a peptide length of 46 residues. Peptide E was generated by V8 protease cleavage of ERRP and was purified by reverse phase HPLC as shown in FIG. 8. 21 and 40 pmol of peptide E were subjected to amino acid analysis.
[b]Composition inferred from cDNA sequence (14).

Iodination of EGF and TGF-alpha. Receptor grade EGF (Upstate Biotechnology, Inc., Lake Placid, N.Y.) and synthetic rat TGF-alpha (Peninsula Lab, Belmont, Calif.) were iodinated with Na[$^{125}$I] (Amersham, Arlington Heights, Ill.) by the chloramine T method (42) to specific activities of $4.0 \times 10^5$ cpm/ng and $3.5 \times 10^5$ cpm/ng, respectively.

Cross-linking and enzymatic digestion. ERRP was incubated with [$^{125}$I]EGF or [$^{125}$I]TGF-alpha at a ratio of 1000:1 (w/w) for 2 hr at room temperature. Disuccinimidyl suberate (DSS) (Pierce Chemical Co., Rockford, Ill.) was added to the final concentration of 1 mM. After 20 min, the reaction was stopped by the addition of reduction and alkylation buffer (1M Tris, pH 8.4, 6M GnHCl and 5 mM EDTA). The detailed procedures for reduction and alkylation were described previously (40). The alkylated cross-linking material was dialyzed in either endoproteinase Glu-C digestion buffer (0.05M $NH_4HCO_3$, pH 7.8) or endoproteinase Lys-C digestion buffer (0.1M $NH_4HCO_3$, pH 9.0). Cleavage by endoproteinase Glu-C (Boehringer-Mannheim, Indianapolis, Ind.) was carried out at an enzyme-protein ratio of 1:40 (w/w) for 14 hours at room temperature, and cleavage by endoproteinase Lys-C (Boehringer-Mannheim) was performed at a ratio of 1:40 (w/w) for 10 hr at 37° C.

Immunoprecipitation of ERRP fragments. The protease activity in digests was inactivated by boiling for 2 min and immunoprecipitation was performed by addition of LA22 IgG$_2$a (43) conjugated to Affi-Gel 10 (BioRad, Richmond, Calif.) (1 mg antibody/ml gel). After a 1½ hr incubation at 22° C., the supernatant was removed, and the gel was washed twice with 1% BSA in PBS and twice by PBS or, for further cleavage, by either Endo Glu-C digestion buffer or Endo Lys-C digestion buffer. The gels washed with digestion buffers were boiled for 2 min to release peptides from the antibodies. Proteases were then added to the gel slurry and incubated for 10 hrs at room temperature for Endo Glu-C and at 37° C. for Endo Lys-C.

Figure 12:
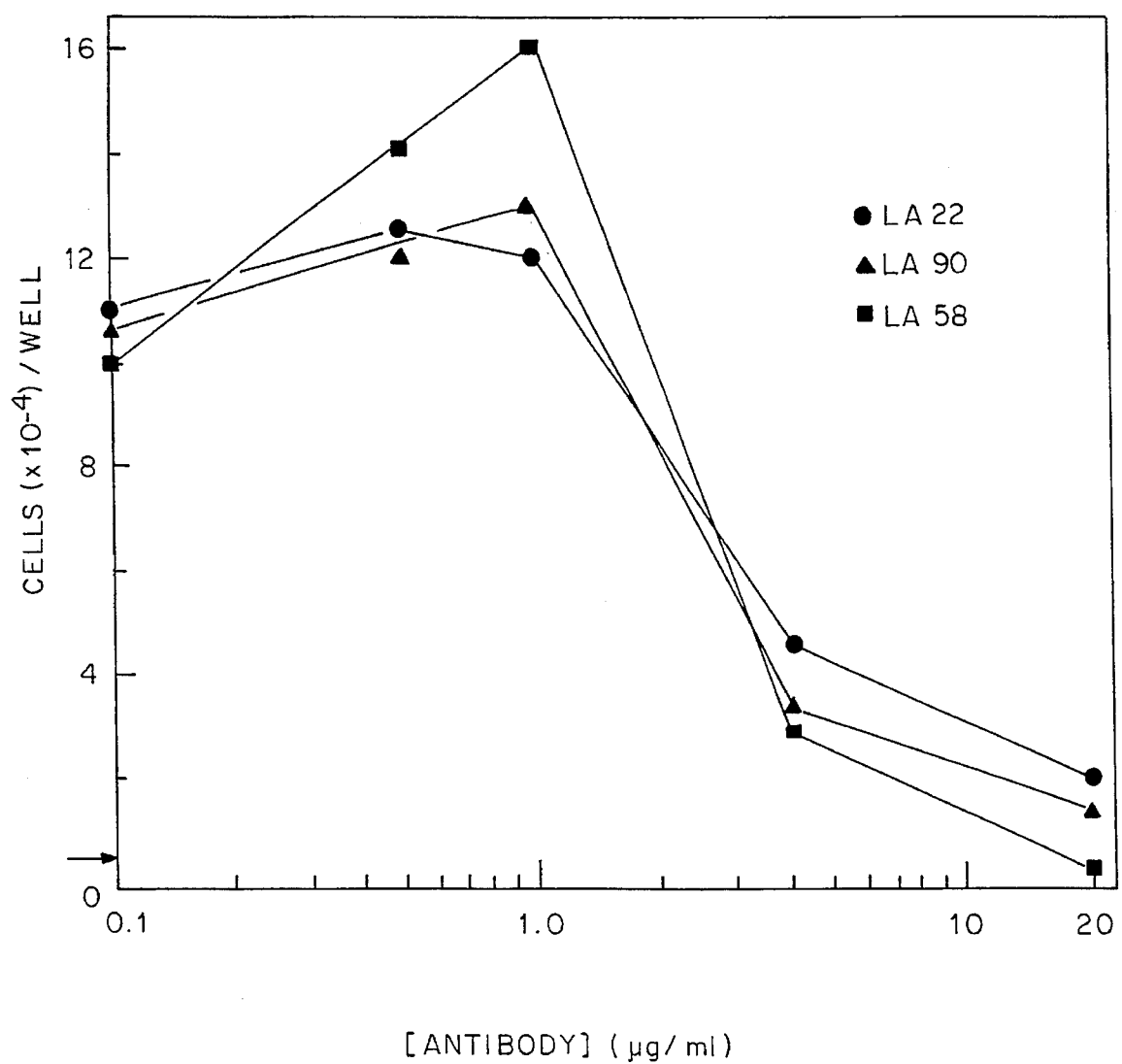
FIG. 12. Inhibition of A431 growth by EGF receptor monoclonal antibodies. A431 cells were seeded in 24-well plates at $5 \times 10^3$ cells/ml in DME/F12 medium, and they were cultured in the presence of increasing concentrations of monoclonal antibodies LA22 (filled in circles ), LA58 (filled in squares ), and LA90 (filled in triangles) for 6 days at 37° C. Cells in duplicate wells were harvested by trypsinization and counted with a Coulter particle counter.

Inhibition of growth of a human tumor cell line A431 cells (22) were plated in 24-well plates (Costar, Cambridge, Mass.) at $5 \times 10^3$ cells/ml in DME/F12 medium. Increasing concentrations of protein A-purified monoclonal antibodies LA22, LA58 and LA90 were added to duplicate wells as indicated in FIG. 12. After a six day incubation at 37° C., the cells were trypsinized and counted with a Coulter Particle counter (Coulter Electronics).

EXAMPLES

Interaction between monoclonal antibodies and the EGF-binding domain of the EGF receptor Three monoclonal antibodies, LA22, LA58, and LA90 were used to study the interaction between EGF and the ligand-binding domain of the human EGF receptor. All three of the antibodies inhibited the binding of $^{125}$I-EGF to A431 human epidermoid carcinoma cells (22) (Table II). In addition, each antibody completely inhibited the binding of the other two antibodies to A431 cells, and the binding of each antibody was inhibited up to 87% by EGF. Furthermore, the binding of all three antibodies was blocked by the EGF-inhibiting monoclonal antibody 528 IgG (33, 34) but not by the oligosaccharide-specific EGF receptor antibody 455 IgG (32). Lineweaver-Burk plots of $^{125}$I-EGF binding to live A431 cells in the presence of 20 nM LA22 or 20 nM LA58 indicated that the antibodies did not detectably alter $B_{max}$ (FIG. 1). Similar results were obtained with $^{125}$I-EGF binding to fixed A431 cells in the presence of antibodies at 66 nM (results not shown). Thus, these antibodies, like 528 IgG (44), mainly inhibited EGF receptor interactions in a competitive manner. These results suggested that the monoclonal antibodies recognized spatially related epitopes and that these antigenic determinants were within, or immediately adjacent to, the receptor EGF-binding site.

TABLE II

Mutually competitive binding of EGF and monoclonal antibodies
Competitive binding assays were done using paraformaldehyde-fixed A431 cells as described under "Experimental Procedures." The concentrations and specific activities of $^{125}$I-labeled ligands were: EGF (0.5 nM, $4.8 \times 10^5$ cpm/ng); LA22 (0.3 nM, $1.5 \times 10^5$ cpm/ng); LA58 (0.4 nM, $8.0 \times 10^4$ cpm/ng); and LA90 (0.3 nM, $9.3 \times 10^4$ cpm/ng). Competing ligands were added to saturating concentrations. The results are expressed as percent maximum inhibition.

| | Competing ligand | | | | | |
| --- | --- | --- | --- | --- | --- | --- |
| $^{125}$I-Ligand | EGF | LA22 | LA58 | LA90 | 528 | 455 |
| EGF | 97 | 87 | 89 | 85 | 97 | 0 |
| LA22 | 87 | 100 | 100 | 100 | 100 | 0 |
| LA58 | 84 | 100 | 100 | 100 | 100 | 0 |
| LA90 | 85 | 100 | 97 | 100 | 98 | 0 |

Interaction of monoclonal antibodies with deglycosylated receptor segments

Western analysis was used to determine whether the antibodies recognized continuous epitopes as opposed to conformational assembly or carbohydrate determinants on EGF receptors. The antibodies were reacted with intact or deglycosylated A431 EGF receptor-related protein (ERRP), a truncated form of EGF receptor that is secreted by A431 cells (26). The receptor-related protein is a $M_r$ 105,000 glycoprotein that binds EGF and includes the entire extracellular domain of the EGF receptor (14). As shown in FIG. 2, all three monoclonal antibodies bound to both the intact and deglycosylated forms of ERRP. In contrast, 455 IgG (31), an EGF receptor monoclonal antibody that recognizes a blood group A-related oligosaccharide epitope (45), bound to intact but not to deglycosylated ERRP (FIG. 2, lanes 6 and 7). These results indicated that LA22, LA90, and LA58 did not recognize endoglycosidase F-sensitive N-linked glycans, and they indicated that the antibodies recognized continuous peptide epitopes.

Further localization of the epitopes recognized by the monoclonal antibodies

Figure 3A:
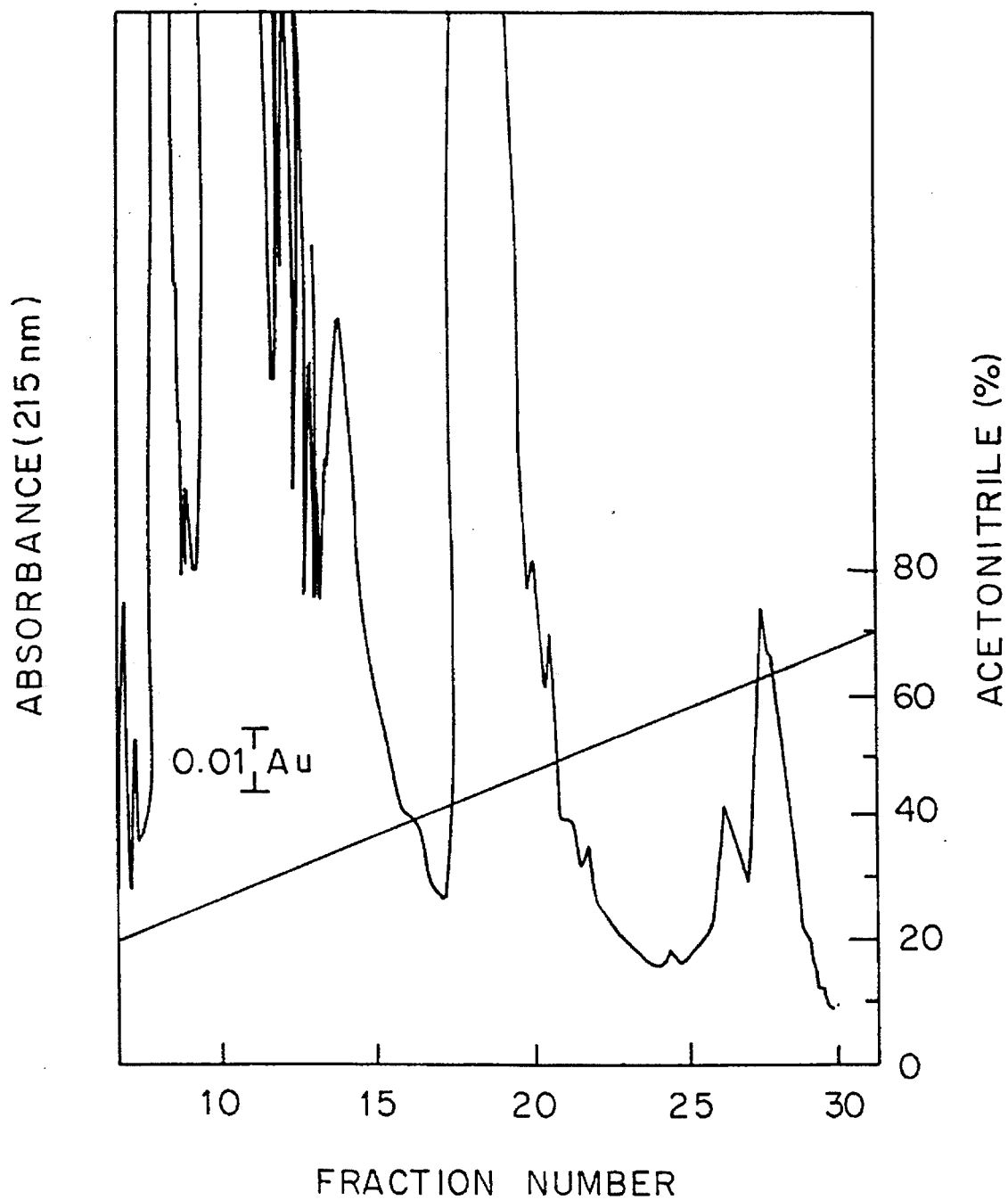
FIG. 3(A) CNBr-generated ERRP fragments were fractionated on a C-4 reverse phase column using a 20–60% gradient of acetonitrile in aqueous 0.1% TFA.
Figure 3B:
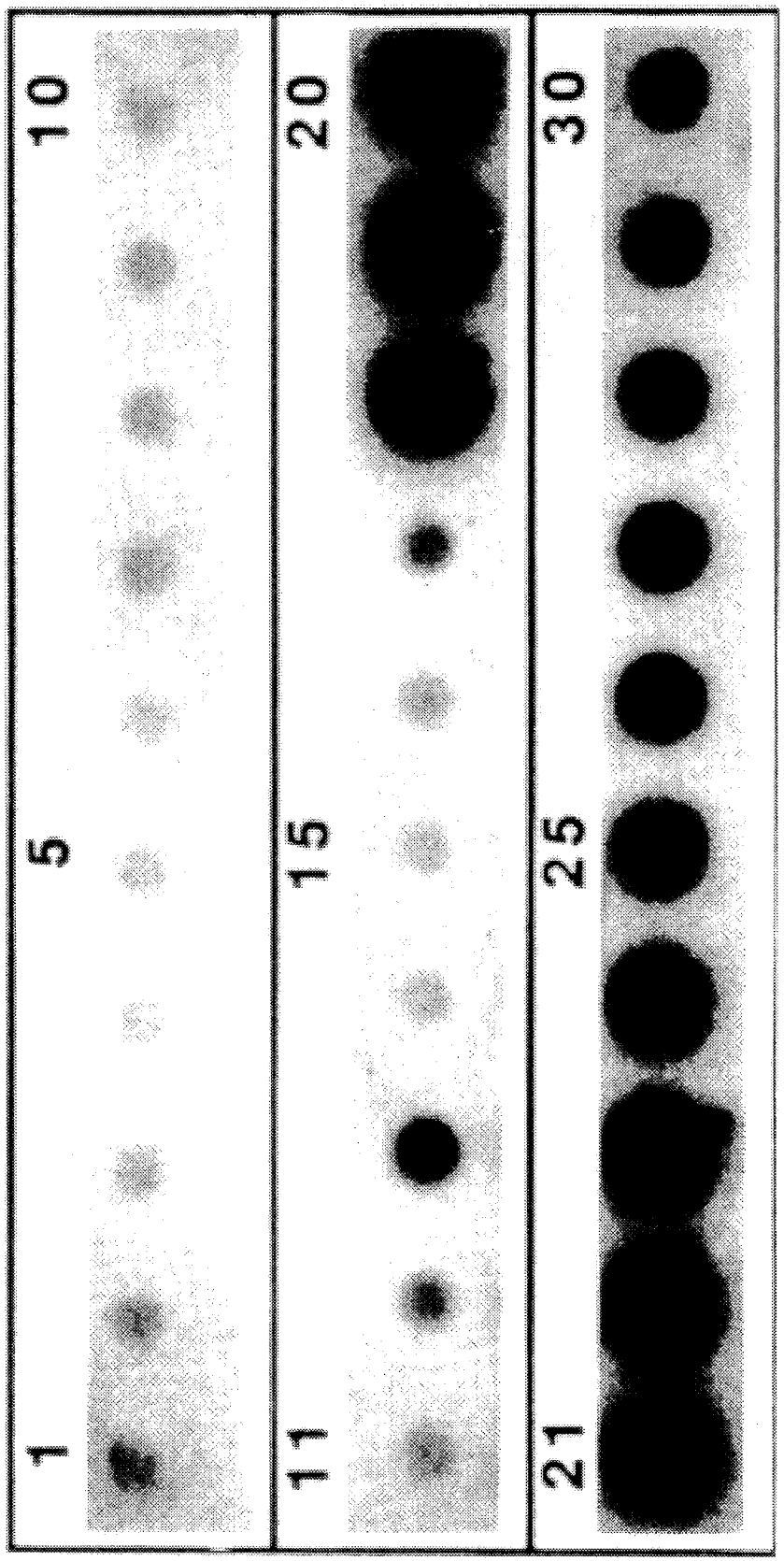
FIG. 3(B) A 10 μl aliquot of each column fraction was reacted with LA22 in a dot blot assay.
Figure 4:
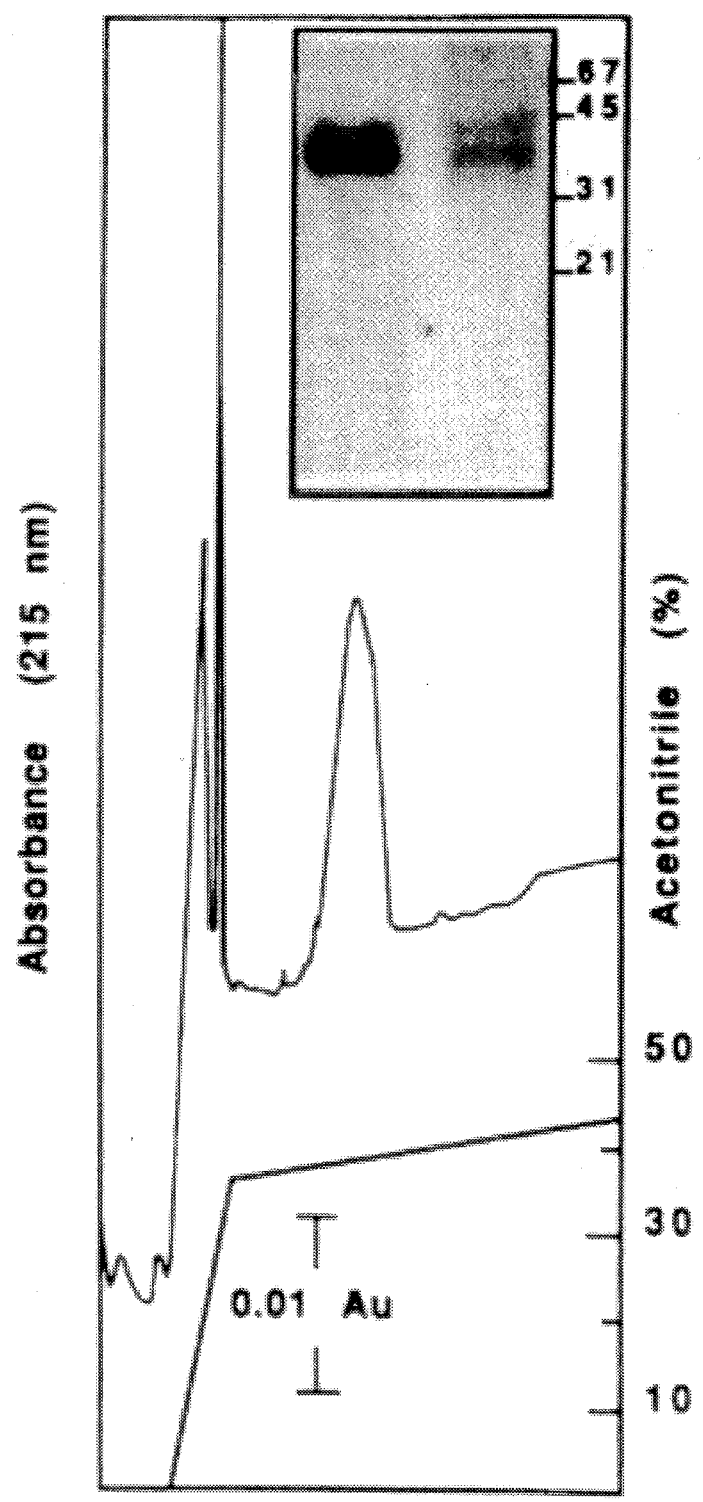
FIG. 4. LA22-reactive $M_r$ 43,000 and $M_r$ 37,000 ERRP fragments. CNBr fragments in fraction 19 (FIG. 3) were rechromatographed on a C-4 reverse phase HPLC column. The main absorbance peak was analyzed by N-terminal sequencing and electrophoresis. Edman degradation yielded a major amino acid sequence of XEDGV and a minor sequence of XXNPE. $M_r$ 43,000 and $M_r$ 37,000 bands were detected after SDS-PAGE in a 15% polyacrylamide gel by silver staining (inset, right lane) and western blotting with LA22 antibodies (inset, left lane).

The ability of the three monoclonal antibodies to react with denatured ERRP was exploited to define the epitopes of these EGF competitive antibodies. Cyanogen bromide (CNBr)-generated fragments of reduced and carboxymethylated ERRP were resolved by reverse-phase HPLC (FIG. 3A), and each fraction was tested for immunoreactivity to LA22 (FIG. 3B). Inspection of the deduced amino acid sequence of ERRP (14) predicted that complete cleavage would generate 11 CNBr fragments ranging in size from 9 to 250 amino acids. As shown in FIG. 3, LA22 IgG reacted most strongly with fractions 19–22 which corresponded to an absorbance peak eluting from the HPLC column between 40–50% acetonitrile. Fraction 19 consisted of a broad peak on reverse-phase HPLC (FIG. 4) which was resolved by SDS-polyacrylamide gel electrophoresis into two immunoreactive bands of $M_r$ 370,000 and 43,000 (FIG. 4, inset). When subjected to amino acid sequencing, this HPLC peak yielded a major sequence (initial yield 38 pmol) starting at Glu-295 (XEDGV..., FIG. 5) and a minor sequence (initial yield 7 pmol) starting with Asp-254 (XXNPE . . .) (14). Fraction 21 (FIG. 3) yielded an additional immunoreactive CNBr peptide of $M_r$ 170,000 (peak C, FIG. 6), which also started with Glu-295 (EEDGV . . . , peptide C; initial yield 28 pmol).

Figure 5:
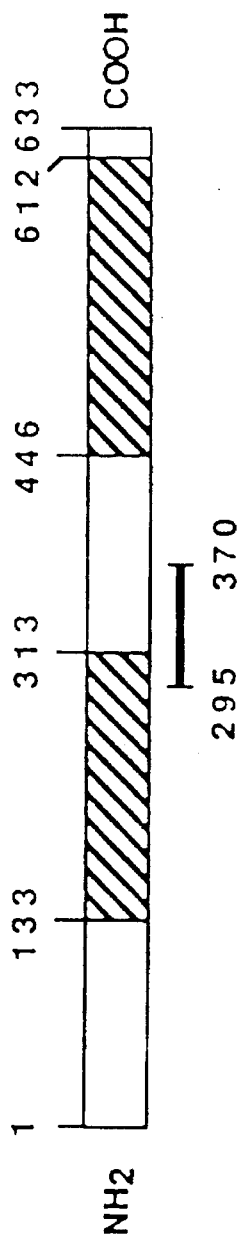
FIG. 5. Schematic representations of the ERRP of A431 cells. The Cysteine-rich regions from Cys-133 to Cys-313 and Cys-446 to Cys-612 are hatched. The amino acid sequence deduced from ERRP cDNA (14) for residues 295 through 370, denoted by the bar, is presented below. Consensus sequences for potential asparagine-linked glycosylation sites are overlined, the Arg-Gly-Asp-Ser adhesion molecule recognition site (27) is boxed, and the 14-amino acid peptide recognized by LA22, LA58, and LA90 is underlined. Amino acid differences in the chicken EGF receptor sequence homologous to residues 295 through 370 of the human receptor (20) are indicated.
Figure 6:
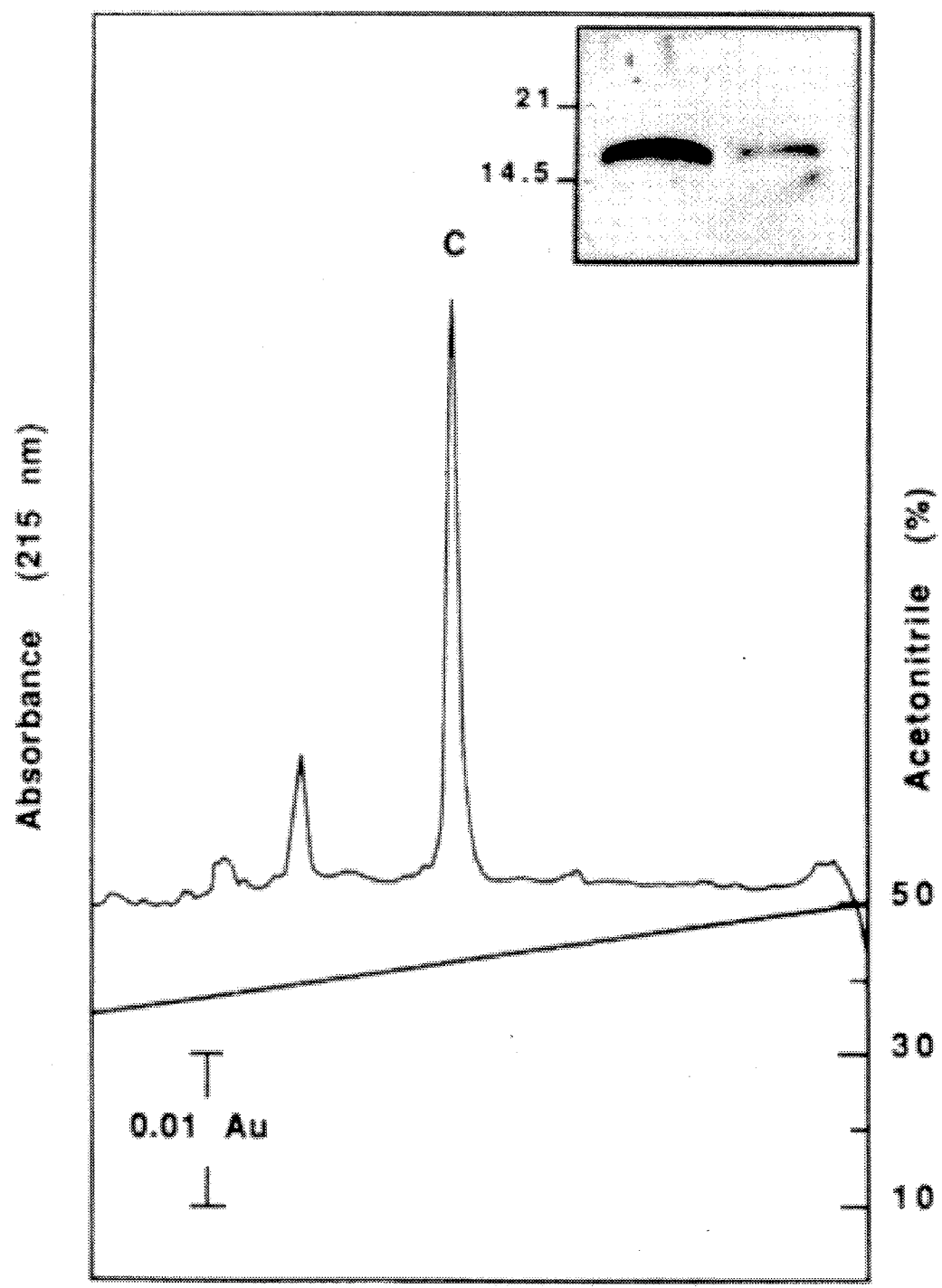
FIG. 6. LA22-reactive $M_r$ 17,000 ERRP fragment. CNBr fragments in fraction 21 (FIG. 3) were rechromatographed on a C-4 reverse phase HPLC column. Peak C was analyzed by N-terminal sequencing and electrophoresis. Edman degradation yielded an amino acid sequence of EEDGV. The $M_r$ 17,000 ERRP fragment was detected after SDS-PAGE by silver staining (inset, right lane) and western blotting with LA22 antibodies (inset, left lane).
Figure 7:
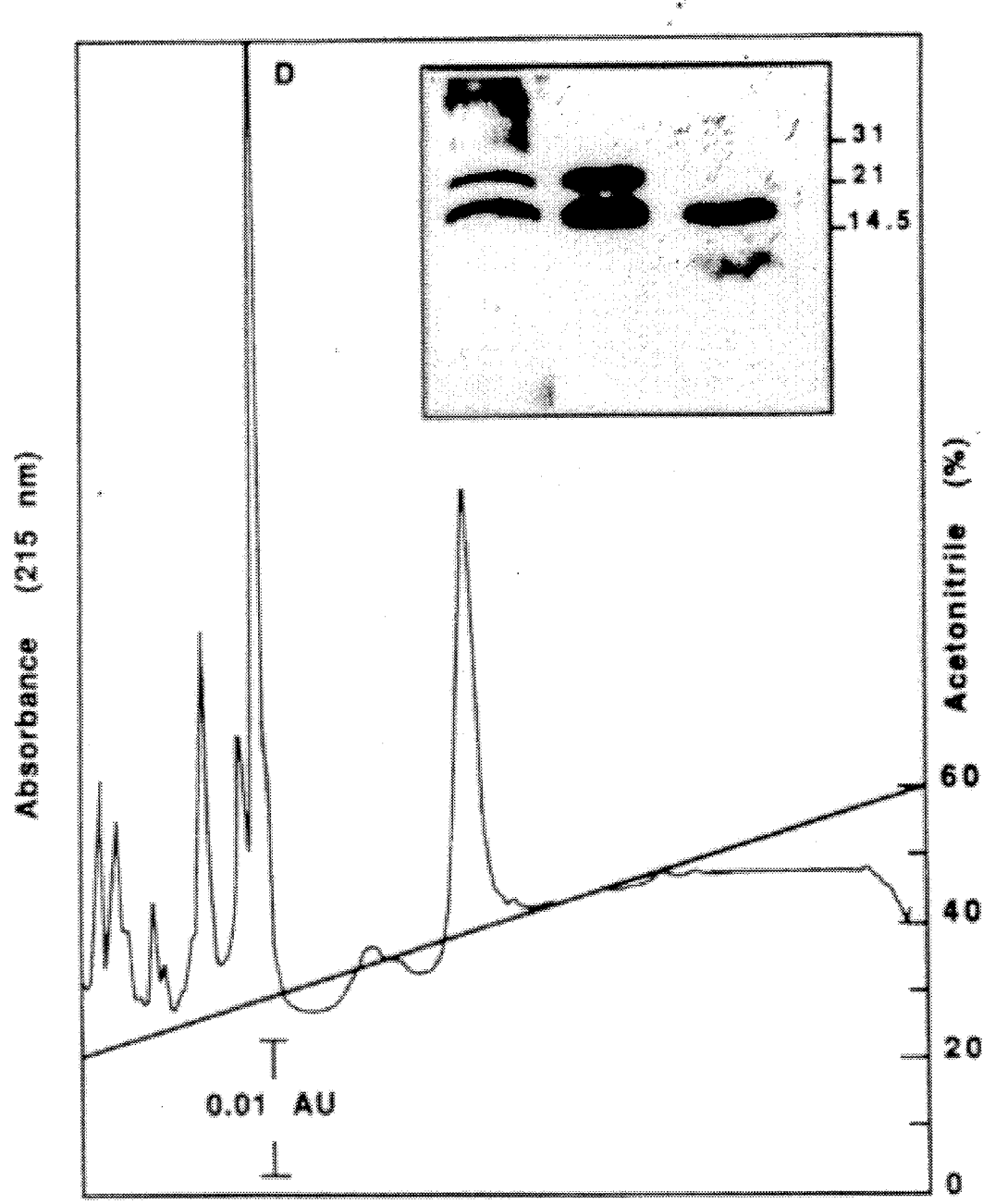
FIG. 7. Reverse phase HPLC chromatography of acid-cleaved $M_r$ 43,000 and $M_r$ 37,000 CNBr fragments of ERRP. The $M_r$ 43,000 and $M_r$ 37,000 CNBr-generated ERRP fragments (FIG. 4) were cleaved with 0.1% trifluoracetic acid (28) and were chromatographed on a C-4 reverse phase column. Peak D, which reacted with LA22 antibodies in a dot blot assay, was analyzed by N-terminal sequencing and electrophoresis. Edman degradation yielded a major amino acid sequence of EEDGVR and a minor sequence of DVNPEG. This peak was resolved by electrophoresis into bands of $M_r$ 23,000 and $M_r$ 17,000 (inset, left lane) that reacted with LA22 antibodies (inset, middle lane). These bands were converted to LA22-reactive bands of lower molecular weight by endoglycosidase F (inset, right lane).

The presence of an acid-labile peptide bond between Asp-364 and Pro-365 (14) suggested that Asp-364 was the COOH-terminal amino acid of the $M_r$ 17,000 CNBr peptide. This possibility was supported by the observation that the $M_r$ 43,000 and 37,000 CNBr fragments (FIG. 4) were converted by acid treatment to $M_r$ 23,000 and 17,000 LA22-reactive polypeptides with conserved $NH_2$-terminal amino acid sequences (FIG. 7). Together these results suggested that the epitope recognized by LA22 resided within the 70 amino acids between Glu-295 and Asp-364 (FIG. 5). This 70-residue peptide had two potential N-linked glycosylation sites at Asn-328 and Asn-337 (14). The difference between the apparent molecular weight of this 70-amino acid peptide ($M_r$ 170,000) and that deduced from its primary structure ($M_r$ 9,200) suggested that the peptide was modified at one or both glycosylation sites. Endoglycosidase F digestion of the $M_r$ 23,000 and 17,000 immunoreactive peptides resulted in molecular weight decreases in both peptides (FIG. 7, inset) indicating that these peptides were indeed glycosylated.

To further localize the epitope recognized by LA22, the $M_r$ 43,000 and 37,000 CNBr peptides (FIG. 4, inset) were cleaved with V8 protease at glutamyl residues (29) generating an $M_r$ 15,000 immunoreactive fragment (peptide E, FIG. 8). Edman degradation of this peptide yielded a sequence starting with Phe-321 (FKDSLSIXATNIKHFKX-CTSI . . . , initial yield 100 pmol). The first 21 amino acids of this peptide were identical to the corresponding amino acid sequence deduced from cloned EGF receptor cDNA (14) FIG. 5) with the exception that no detectable PTH yields were obtained for Asn-329 and Asn-337. These results further suggested that both asparagine residues were glycosylated. Based on the cleavage specificity of V8 protease and the molecular weight of peptide E, the COOH-terminal amino acid of this peptide was predicted to be Glu-367. This prediction was confirmed by amino acid analysis (Table I): the amino acid composition of the $M_r$ 15,000 peptide was virtually identical to the known amino acid composition of the 47-residue sequence from Phe-321 to Glu-367 (14) (FIG. 5).

Figure 9A:
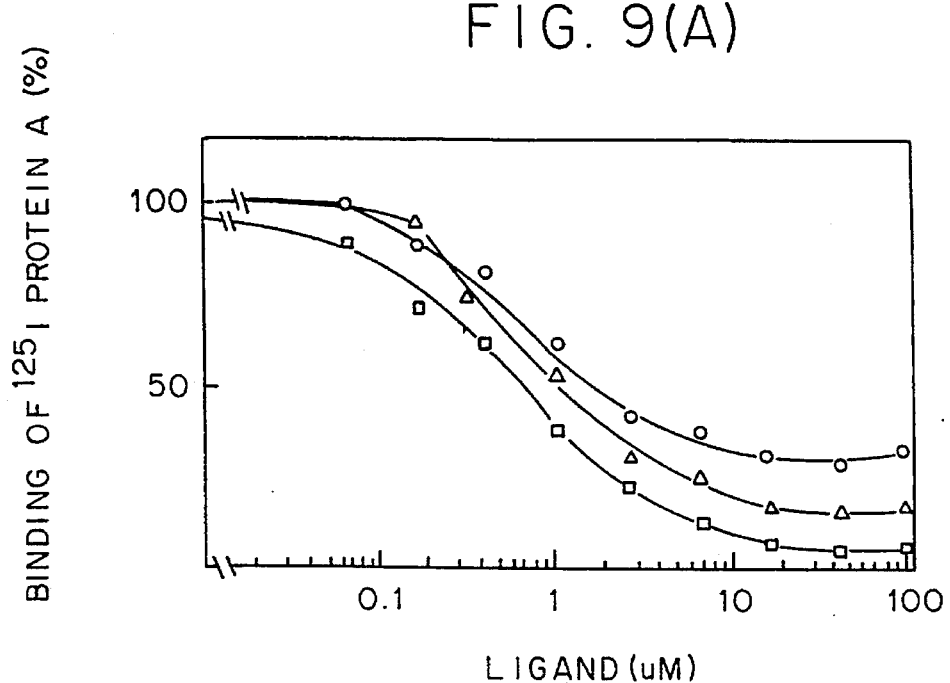
FIG. 9. Inhibition of antibody binding to ERRP by synthetic peptides. Synthetic peptides of 24 residues (FIG. 9A) and 14 residues (FIG. 9B) corresponding to EGF receptor sequences Asp-344 to Glu-367 and Ala-351 to Asp-364 (FIG. 4) (14), respectively, were used to inhibit the binding of purified LA22 (FIG. 9A, triangles.
FIG. 9B,open circles), LA58 (FIG. 9A, circles; B,squares), and LA90 (FIG. 9A; squares, FIG. 9B,triangles) to immobilized ERRP. The inhibition of LA22 binding by purified ERRP (filled in circles) is presented in panel B.
Figure 9B:
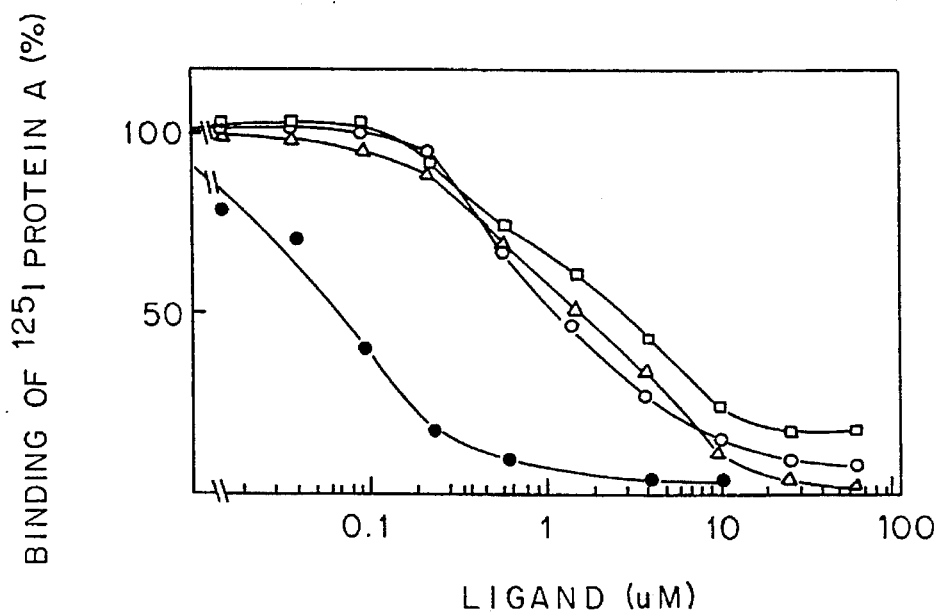

Analyses of peptides C and E suggested that the epitope for LA22 resided within the 44 amino acids from Phe-321 to Asp-364 (FIG. 5). Preliminary experiments indicated that the reactivity of LA22 for ERRP was abolished by Arg-C endoproteinase (data not shown). Since Arg-353 was the sole arginine residue between Phe-21 and Asp-364 (14) (FIG. 5), it was likely that the epitope for LA22 was within the COOH-terminal portion of this 44-residue amino acid sequence. Therefore, a 24-residue peptide was synthesized based upon the receptor sequence from Asp-344 to Glu-367, which included the Arg-Gly-Asp-Ser adhesion molecule receptor recognition sequence (27) at residues 353–356. The synthetic 24-mer inhibited the binding of antibodies-LA22, LA58, and LA90 to immobilized ERRP (FIG. 9A); the concentration of the 24-mer needed to inhibit antibody binding by 50% ranged from 0.7 to 2 μM. These results demonstrated that these three mutually competitive antibodies (Table II) recognized closely spaced and perhaps identical antigenic determinants. A synthetic 14-residue peptide, Ala-351 to Asp-364 (FIG. 5), within the 24-mer sequence also effectively inhibited the binding of all three antibodies to ERRP (FIG. 9B) with half-maximal inhibition occurring at concentrations of 1–3 μM. Both synthetic peptides were 10- to 50-fold less effective than intact ERRP in inhibiting antibody binding. Although both peptides included the recognition sequence for adhesion molecule receptors, a synthetic Arg-Gly-Asp-Ser tetramer had no effect on antibody binding to ERRP (data not shown). From these results the epitopes for the EGF competitive antibodies LA22, LA58, and LA90 were assigned to a region of the EGF receptor extra-cellular domain not larger than 14 amino acids, which was flanked by the two cysteine-rich sequences at residues 134–313 and 446–612(14). The antibody reactive synthetic peptides neither bound $^{125}I$-EGF when immobilized on a plastic substrate nor inhibited $^{125}I$-EGF binding to A431 cells (results not shown). Thus, the epitopes for antibodies LA22, LA58, and LA90 did not comprise the entire ligand-binding region of the human EGF receptor.

Discussion of the foregoing results

We have used the truncated M, 105,000 form of the EGF receptor secreted by A431 human epidermoid carcinoma cells (26) to define the epitopes of three EGF competitive monoclonal antibodies. The truncated receptor (ERRP) is identical in sequence to the extra-cellular domain of the full length human EGF receptor, but it includes 17 nonidentical COOH-terminal amino acids starting from residue 617 (14). This form of the EGF receptor is encoded by an overexpressed 2.8-kb mRNA in A431 cells (14).

The monoclonal antibodies under study were raised against intact A431 cells and A431 membrane preparations, and they were selected for the ability to inhibit $^{125}I$-EGF binding to A431 cells. The antibodies LA22, LA58, and LA90 were mutually inhibitory, and they were largely inhibited by EGF in binding to A431 cells (Table II). These three antibodies were therefore, to that extent, similar in their binding properties to the EGF receptor monoclonal antibodies 528, 225, and 579 (31,34) and distinct from receptor antibody 455 which bound to an oligosaccharide determinant without inhibiting EGF binding (31,45). The binding of LA22, LA58, and LA90 to A431 cells was completely inhibited by 528 IgG but was not affected by 455 IgG (Table II). Like 528 IgG (44), these antibodies were competitive inhibitors of EGF receptor interactions (FIG. 1).

Unlike previously reported EGF competitive monoclonal antibodies (23,31,46), LA22, LA58, and LA90 recognized both denatured and deglycosylated forms of the EGF receptor (FIG. 2). These properties enabled us to analyze the binding of these antibodies to CNB4- and protease-generated ERRP peptides. Based on the recognition by LA22 of ERRP peptide C, a 70-amino acid fragment, and peptide E, a 47-amino acid V8 protease-generated ERRP peptide, the epitope for LA22 was localized to the 44 amino acids between Phe-321 and Asp-364 (FIG. 5). Inhibition of the binding of LA22, LA58, and LA90 to ERRP by synthetic peptides (FIG. 9) placed the epitopes for these antibodies within the 14 amino acids from Ala-351 to Asp-364 (FIG. 5). Thus, these three EGF competitive antibodies recognized closely spaced amino acid determinants within a very limited region of the extra-cellular domain of the EGF receptor. This region of the receptor is located between the two cysteine-rich regions that span residues 134–313 and residues 446–612 (14).

Although antibodies LA22, LA58, and LA90 bound to a short region of the EGF receptor, it remained possible that they recognized adjacent or overlapping epitopes (47). Studies with synthetic peptide immunogens have indicated that peptides of fewer than 10 amino acids are generally poor immunogens and that the optimum length for immunogenic peptides is 10–15 amino acids (48,49). These findings suggested that the 14-amino acid sequence of the EGF receptor that bound all three antibodies comprised but a single antigenic determinant and that the antibodies had identical antigenic specificities. An Arg-Gly-Asp-Ser recognition site for adhesion molecule receptors occurred with the NH$_2$-terminal half of the antibody-binding 14-mer at receptor residues 353–356 (14). Whether or not this sequence of amino acids can mediate the binding of receptors for fibronectin or other adhesion molecules to EGF receptors is unknown (27). The Arg-Gly-Asp-Ser tetramer was reported to inhibit the attachment of normal rat kidney cells to fibronectin-coated plastic (50), but it did not inhibit the binding of any of the antibodies to immobilized ERRP. Thus, this tetramer does not by itself constitute the epitope recognized by these antibodies. However, we cannot rule out the possibility that it is an integral part of the epitope.

The 14-residue human EGF receptor epitope described here is 71.4% identical to the homologous region of the chicken EGF receptor (Ala-352 to Asp-365) (20). Of the four amino acid differences between the two sequences, two occur in the adhesion receptor recognition tetramer such that the human Arg-Gly-Asp-Ser sequence corresponds to Leu-Gly-Asp-Ala in the chicken receptor (20). The remaining two amino acid differences occur at residues 359 (His to Lys) and 361 (Pro to Leu) of the human receptor (14,20) (FIG. 5). These amino acid alterations may help to explain the 100-fold difference in the affinities of human and chicken EGF receptors of murine EGF (20).

Our results with EGF competitive antibodies are consistent with and extend those of Lax et al (25) who reported that EGF could be covalently cross-linked to the EGF receptor between Met-294 and Asn-544. We have further found, as described below that immobilized LA22 IgG precipitated a $M_r$ 18,000 V8 protease-generated ERRP fragment cross-linked to $^{125}$I-EGF which suggested that the epitope for the monoclonal antibodies and the receptor residue(s) covalently linked to EGF colocalized to the 47 amino acids of ERRP peptide E (FIG. 8) (51). The locations of the cysteine-rich regions in the primary structure of the EGF receptor (14) suggest that the native conformation of the extra-cellular domain is of vital importance for the binding of EGF (25) and most EGF competitive antibodies (23). The smallest antibody-reactive synthetic peptide described here does not bind EGF. However, the mutually competitive binding properties of LA22, LA58, LA90, and EGF strongly imply that the 14-amino acid region of the receptor between Ala-351 and Asp-364 participates in the formation of the EGF-binding site. This conclusion supports a model of EGF receptor structure in which a ligand-binding cleft is formed between the two cysteine-rich regions of the extra-cellular domain.

Figure 10:
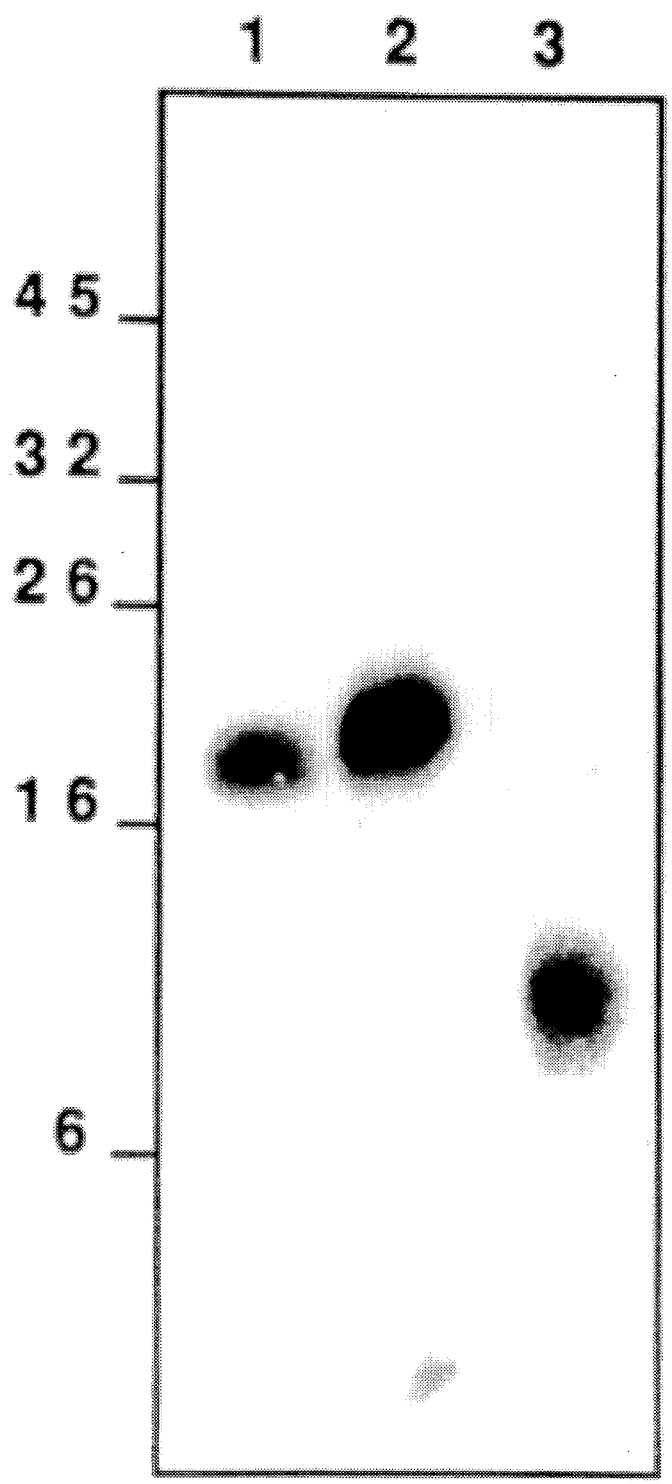
FIG. 10. Immunoprecipitaton of the cross-linked fragments produced from [$^{125}$I]EGF-ERRP complexes by Endo-Glu-C. The reduced and carboxymethylated cross-linking complex was digested by Endo Glu-C and immunoprecipitated by immobilized LA22. The immunoprecipitated fragments was either run on 15% SDS-PAGE (lane 1) or subjected to further treatment with Endo Glu-C (lane 2) or Endo-F (lane 3) prior to electrophoresis. The dried gel was exposed to X-ray film.

Localization of a Receptor Residue That Can Be Cross-linked to a Receptor-bound EGF ERRP secreted by A431 cells contains the entire extra-cellular domain of the EGF receptor (14). To identify receptor cross-linking sites, [$^{125}$I]EGF was covalently cross-linked to ERRP with DSS, and the [$^{125}$I]EGF-ERRP complex was cleaved by proteases. The reduced and alkylated [$^{125}$I]EGF-ERRP complex was first digested with endoproteinase Glu-C (Endo Glu-C), an enzyme that specifically cleaves at the carboxyl side of glutamyl residues (29). The enzyme was then heat-inactivated and the cleavage products were immunoprecipitated with immobilized LA22. Bound peptides were released by boiling in SDS-PAGE sample buffer and were analyzed by electrophoresis and autoradiography. A single radiolabeled $M_r$ 18,000 band was detected (FIG. 10, lane 1). This indicated that the epitope of LA22 was in close proximity to the cross-linked receptor residue(s). To ensure complete cleavage, the $M_r$ 18,000 fragment was treated again with Endo Glu-C. No further shift in mobility or decrease in the intensity of the band was observed (FIG. 10, lane 2).

As noted above, the smallest Endo Glu-C ERRP fragment which contained the LA22 epitope consisted of the 47 amino acids from Phe-321 to Glu-367; this $M_r$ 15,000 peptide included about $M_r$ 9,000 in N-linked carbohydrates distributed between Asn-328 and Asn-337. The $M_r$ 18,000 fragment observed here most likely consisted of this 47 amino acid peptide with a further $M_r$ 3,000 contributed by EGF residues Asn-1 to Glu-24. To confirm this idea, the $M_r$ 18,000 fragment was treated with a mixture of endoglycosidase F and N-glycosidase F (Endo-F). Endo-F treatment reduced molecular weight of the radiolabeled fragment by about $M_r$ 9,000 (FIG. 10, lane 3). This result was consistent with our previous observation that the Endo Glu-C fragment was shifted from $M_r$ 15,000 to $M_r$ 6,000 by Endo-F treatment (43).

Figure 11:
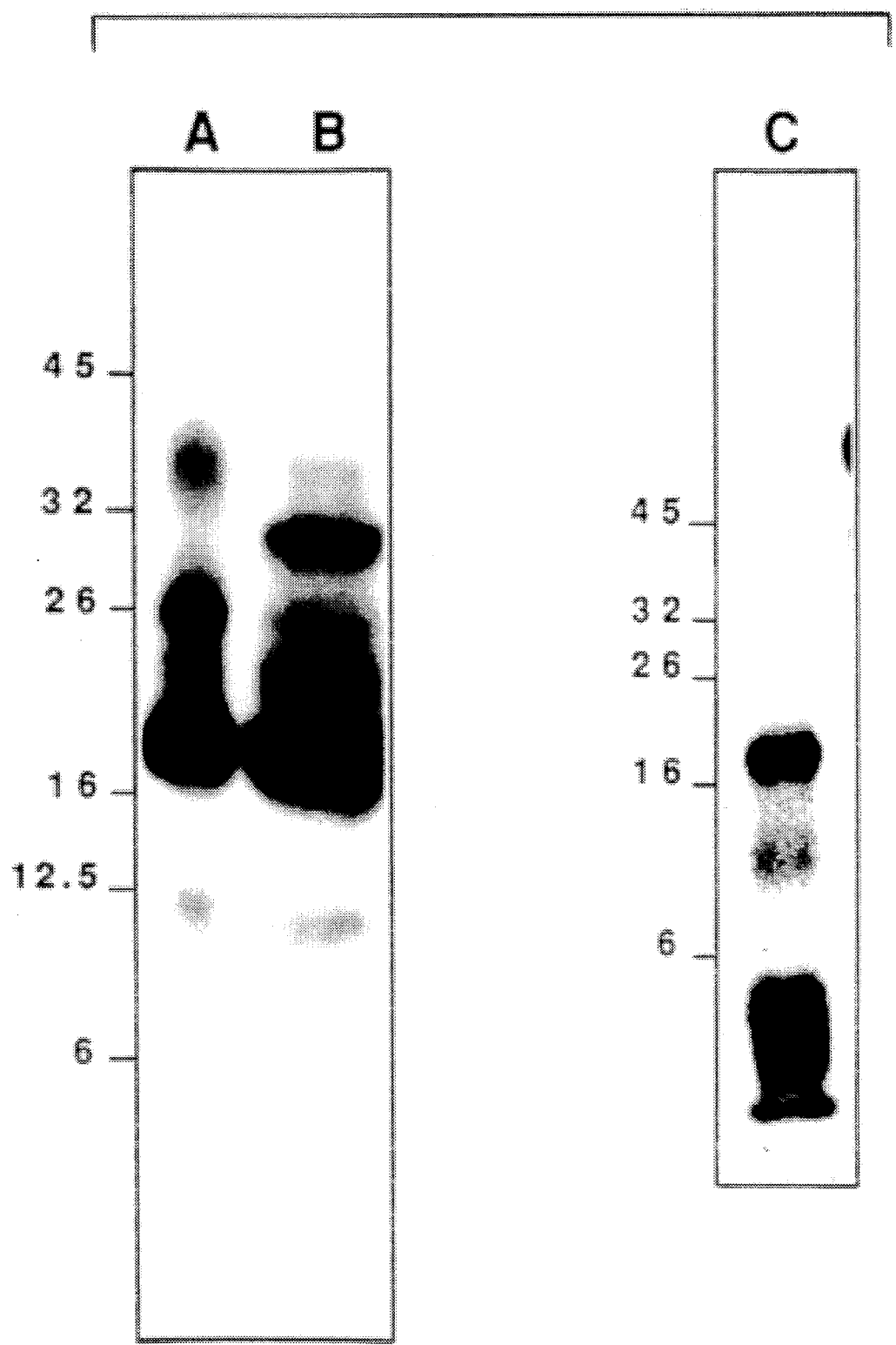
FIG. 11. Cleavage of [$^{125}$I]EGF-ERRP complexes by Endo Lys-C. Reduced and carboxymethylated cross-linked complexes were subjected to cleavage by Endo Lys-C. The resulting fragments were immunoprecipitated by immobilized LA22, and the immunoprecipitate was either directly run on 15% SDS-PAGE (FIG. 11A, lane A), or further treated with Endo-F (FIG. 11A, lane B) or Endo Glu-C (FIG. 11B, lane C), respectively, before electrophoresis. The dried gel was exposed to X-ray film.

According to the amino acid sequence deduced from cloned EGF receptor cDNA (14), this 47 amino acid fragment includes only three lysine residues, Lys-332, Lys-333 and Lys-336, which are potentially available to react with the amine-specific crosslinker DSS. To determine which of these residues were cross-linked to EGF, [$^{125}$I]EGF-ERRP complexes were cleaved with endoproteinase Lys-C (Endo Lys-C), which specifically cleaves peptide bonds on the carboxyl side of lysyl residues (52). At least five LA22-reactive radiolabeled fragments were detected (FIG. 11, lane A), which indicated that the digestion was incomplete. The two smallest Endo Lys-C fragments immunoprecipitated by immobilized LA22 antibodies were a peptide of approximately $M_r$ 12,500 and a prominent radiolabeled $M_r$ 18,000 peptide. When deglycosylated with Endo F, both bands shifted in molecular weight by approximately $M_r$ 1–2,000 (FIG. 11, lane B). As this shift in molecular weight did not equal or exceed $M_r$ 9,000, it was evident that both ERRP fragments contained only a single glycosylated residue, Asn-337, which was the most proximal to the LA22 epitope (Ala-351 to Asp-364) of the two glycosylation sites between Phe-321 and Glu-367. This experiment further indicated that the oligosaccharides N-linked to Asn-328 and Asn-337 contributed to $M_r$ 7–8,000 and $M_r$ 1–2,000, respectively, to the mass of ERRP.

Since the $NH_2$-termini of the $M_r$ 12,500 and the $M_r$ 18,000 ERRP fragments resided between Asn-328 and Asn-337, the cleavage specificity of Endo Lys-C indicated that His-334 was the $NH_2$-terminal residue of both fragments and that Lys-336 was the sole receptor residue that could be cross-linked by DSS to EGF. As EGF possesses no lysyl residues, it is most likely cross-linked to ERRP via the amino group of Asn-1. Although the COOH-terminal residues of the ERRP fragments could not be identified unambiguously, the molecular masses of the [$^{125}$I]EGF-peptide complexes were consistent with the $M_r$ 12,500 fragment terminating with Lys- 372 or Lys-375 and the $M_r$ 18,000 fragment ending at Lys- 407. The existence of the radiolabeled $M_r$ 18,000 fragment suggested that the cleavage of ERRP by Endo Lys-C at residues 372 and 375 was very inefficient.

To eliminate the possibility that cleavage by Endo Lys-C was occurring at residues other than lysine, the immunoprecipitated fragments generated with Endo Lys-C were digested with Endo Glu-C. Three radiolabeled fragments were expected if Endo Lys-C were acting in a specific manner: an $M_r$ 18,000 band corresponding to receptor fragments from either Phe-321 or Asp-323 to Glu-367, which would result from any fragment bearing the LA22 epitope terminating N-terminal to Lys-333 and C-terminal to Lys-372; and $M_r$ 9,000 receptor fragment corresponding to His-334 to Glu-367, which would be produced from fragments with His-334 as the $NH_2$-terminal amino acid and any lysyl residue at the COOH-terminus; and a $M_r$ 3,000 peptide representing EGF residues 25 to 53 that would be released by the protease. The Endo Glu-C digest was resolved by SDS-PAGE into three bands of $M_r$ 18,000, $M_r$ 9,500 and $M_r$ 3,000 (FIG. 11, lane C). Thus, the original Endo Lys-C cleavages occurred specifically at lysyl residues even though the reaction did not go to completion.

We applied the same strategy to investigate the EGF receptor binding site for TGF-alpha. After cross-linking [$^{125}$I]TGF-alpha to ERRP with DSS, the complex was subjected to reduction and alkylation and Endo Glu-C cleavage. An $M_r$ 18,500 band was detected by autoradiography after immunoprecipitation with LA22 antibodies. Complete cleavage was confirmed by the lack of further digestion with additional Endo Glu-C. This antibody-reactive Endo Glu-C-generated ERRP fragment was most likely the same as that cross-linked with EGF. That is, the band was composed of the Mr 15,000 forty-seven residue receptor fragment Phe-321 to Gln-367 with a $M_r$=3,000 TGF-alpha fragment from Val-1 to Gln-26 or Lys-29 to Ala-50. These data indicated that the receptor site cross-linked with TGF-alpha was also in close proximity to the LA22 epitope and was included within the same 47 amino acid ERRP fragment.

Inhibition of growth of a human tumor cell line

The EGF receptor monoclonal antibodies LA22, LA58 and LA90 were tested for the ability to inhibit the growth in vitro of A431 human epidermoid carcinoma cells (22), which contain a large number of EGF receptors. After a 6 day incubation period at 37° C., all three antibodies at concentrations greater than 1 µg/ml severely inhibited A431 proliferation (FIG. 12). In the presence of 20 µg/ml of each antibody there was essentially no increase in cell number.

EGF receptor antibodies seem to be most effective against tumor cells that express an abnormally high number of EGF receptors. This situation occurs frequently, but not always, in squamous cell carcinomas, non-neuronal brain tumors, breast cancers, and gastric carcinomas. Such antibodies are not, however, effective against all tumors that express EGF receptors.

Monoclonal antibodies can be delivered to a patient through either the blood stream or peritoneal cavity and can be delivered directly to the tumor site. A preferred embodiment would be chimeric antibodies in which the variable region of the mouse heavy and light chains are spliced through recombinant DNA technology to C regions of human heavy and light chains.

REFERENCES

1. James, R., and Bradshaw, R. A. (1984) Annu. Rev. Biochem. 53, 59–292.

2. Carpenter, G. (1987) Annu. Rev. Biochem, 56, 881–914.

3. Gill, G. N., Bertics, P. J., and Stanton, J. B. (1987) Mol. Cell. Endocrinol. 51, 169–186.

4. Yarden, Y., and Ullrich, A. (1988) Biochemistry 27, 3113–3119.

5. Schlessinger, J. (1988) Biochemistry 27, 3119–3123.

6. Savage, C. R., Jr., Inagami, T., and Cohen, S. (1972) J. Biol. Chem. 247, 7612–7621.

7. Savage, C. R., Jr., Hash, J. H., and Cohen, S. (1973) J. Biol. Chem, 247, 7669–7672.

8. Carpenter, G., and Cohen, S. (1979) Annu. Rev. Biochem. 193–216.

9. Gray, A., Dull, T. J., and Ullrich, A. (1983) Nature 303., 722–725.

10. Scott, J., Urdea, M., Quiroga, M., Sanchez-Pescador, R., Fong, N., Selby, M., Rutter, W. J., and Bell, G. I. (1983) Science 221, 236–240.

11. Cohen, S., Carpenter, G., and King, L., Jr. (198) J. Biol Chem. 255, 4834–4842.

12. Ushiro, H., and Cohen, S. (1980) J. Biol. Chem 255, 8363–8365.

13. Buhrow, S. A., Cohen, S., and Staros, J. V. (1982) J. Biol. Chem. 257, 4019–4022.

14. Ullrich, A., Coussens, L., Hayflick, J. S., Dull, T. J., Gray, A., Tem, A. W., Lee, J., Yarden, Y., Libermann, T. A. Schlessinger, J., Downward, J., Mayes, E. L. V., Whittle, N., Waterfield, M. D., and Seeburg, P. H. (1984) Nature 309, 418–425.

15. Mayes, E., and Waterfield, M. D. (1984) EMBO J. 3, 531–537.

16. Childs, R. A., Gregoriou, M., Scudder, P., Thorpe, S. J., Rees, A., and Feizi, T. (1984) EMBO J. 3, 2227–2233.

17. Cummings, R. D., Soderquist, A. M., and Carpenter, G. (1985) J. Biol. Chem. 260, 11944–11952.

18. Weber, W., Bertics, P. J., and Gill, G. N. (1984) J. Biol. Chem. 259, 14631–13636.

19. Downward, J., Parker, P., and Waterfield, M. D. (1984) Nature 311, 483–485.

20. Lax, I., Johnson, A., Howk, R., Sap, J., Bellot, F., Winkler, M., Ullrich, A., Vennstrom, B., Schlessinger, J., and Givol, D. (1988) Moll Cell Biol. 8, 1970–1978.

21. Carpenter, G., and Cohen, S. (1977) Biochem. Biophys. Res. Commun. 79, 545–552.

22. Fabricant, R. N., DeLarco, J. E., and Todaro, G. (1977) Proc. Natl. Acad. Sci. U.S.A. 74, 565–569.

23. Sato, J. D., Le, A., and Kawamoto, T. (1987) Methods Enzymol. 146, 63–81.

24. Slieker, L. J., Martensen, T. M., and Lane, M. D. (1986) J. Biol. Chem. 261, 15233–15241.

25. Lax, I., Burgess, W. H., Bellot, F., Ullrich, A., Schlessinger, J., and Givol, D. (1988) Mol. Cell. Biol. 8, 1831–1834.

26. Weber, W., Gill, G. N., and Spiess, J. (1984) Science 224, 294–297.

27. Rouslahti, E., and Pierschbacher, M. D. (1986) Cell 44, 517–518.

28. Tarr, G. E. (1986) Methods of Protein Microcharacterization, A Practical Handbook (Shively, J. E., ed.) pp. 155–194, Humana Press, Clifton, N.J.)

29. Houmard, J. and Drapeau, G. R. (1972) Proc. Natl. Acad. Sci. 69:3506–3509.

30. Kearney, J. F., Radbruch, A., Liesgang, B., and Rajewsky, K. (1979) J. Immunol. 123, 1548–1550.

31. Sato, J. D., Kawamoto, T., Le, A., Mendelsohn, J., Polikoff, J., and Sato, G. H. (1983) Mol. Bio. Med. 1, 511–529.

32. Kawamoto, T., Sato, J. D., Le, A., McClure, D. B., and Sato, G. H. (1983) Anal. Biochem. 130, 445–453.

33. Sato, J. D., Kawamoto, T., and Okamoto, T. (1987) J. Exp. Med. 165, 1761–1766.

34. Kawamoto, T., Sato, J. D., Le, A., Polikoff, J., Sato G. H., and Mendelson, J. (1983) Proc. Natl. Acad. Sci. USA 80:1337–1341.

35. Ey, P. L., Prowse, S. J., and Jenkin, C. R. (1978). Immunochem. 15:429–436.

36. Burnette, W. N. (1981) Anal. Biochem. 112:195–203.

37. Laemli, U. K. (1970) Nature 227:680–685.

38. Janregni-Adell, J., and Marti, J. (1975) Anal. Biochem. 69:468–473.

39. Mole, J. E., Bhown, A. S. and Bennett, J. C. (1977) J. Immunol. 118:67–70.

40. Crabb, J. W., Johnson, C. W., Carr, S. A., Armes, L. G., and Saari, J. C. (1988) J. Biol. Chem. 263:18678–18687.

41. Merrifield, R. B. (1963) J. Am. Chem. Soc. 85:2149–2154.

42. Hunter, W. M., and Greenwood, F. C. (1962) Nature 194:495–496.

43. Wu, D., Want, L., Sato. G. H., West, K. A., Harris, W. R., Crabb, J. W. and Sato, J. D. (1989) J. Biol. Chem. 264:17469–17475.

44. Gill, G. N., Kawamoto, T., Cochet, C., Le, A., Sato, J. D., Masui, H., McLeod, C., and Mendelson, J. (1984) J. Biol. Chem. 259:7755–7760.

45. Gooi, H. C., Hounsell, E. F., Lax, I., Kris, R. M., Libermann, T. A., Schlessinger, J., Sato, J. D., Kawamoto, T., Mendelsohn, J., and Feizi, T. (1985) Biosci. Rep. 5;83–94.

46. Murthy U., Basu, A., Rodeck, U., Herlyn, M., Ross, A. H., and Das, M. (1987). Arch. Biochem. Biophys. 252:549–560.

47. Benjamin, D. C., Berzofsky, J. A., East, I. J., Gurd, F. R. N., Hannum, C., Leach, S. J., Margoliash, E., Michael, J. G., Miller, A., Prager, E. M., Reichlin, M., Sercarz, E. E., Smith-Gill, S. J., Todd, P. E., and Wilson, A. C. (1984) Annu. Rev. Immunol. 2:67–101.

48. Palfreyman, J. W., Aitchenson, T. C., and Taylor, P. (1984) J. Immunol. Methods 88:149–161.

49. Walter, G. (1986). J. Immunol. Methods 88;149–161.

50. Pierschbacher, M. D. and Ruoslahti, E. (1984) Nature 309:30–33.

51. Wu, D., Wang L., Chi, Y., Sato, G. H., and Sato, J. D. (1990) Submitted for publication.

52. Jekel, P. A., Weijer,, and Beinteme, J.(1983) Anal. Biochem. 134:347–354.

What is claimed is:

1. A monoclonal antibody that competes with EGF for binding to the natural EGF receptor and binds to an epitope between residues Ala-351 and Asp-364 of the natural EGF receptor, which epitope remains immunogenically active after denaturation by each of boiling, treatment with a strong detergent and treatment with a reducing agent.

2. A monoclonal antibody in accordance with claim 1, which binds to the same epitope as the monoclonal antibody produced by a hybridoma selected from the group consisting of hybridoma ATCC HB 10342, hybridoma ATCC HB 10343, and hybridoma ATCC HB 10344.

3. A monoclonal antibody that binds to the same epitope as an antibody selected from the group consisting of LA22, produced by the hybridoma deposited under ATCC accession number HB 10342, LA90 produced by the hybridoma deposited under ATCC accession number HB 10344 and LA58 produced by the hybridoma deposited under ATCC accession number HB 10343, wherein said epitope located on the human EGF receptor between residues Ala-351 and Asp-364, and remains immunogenically active after denaturation by each of boiling, treatment with a strong detergent and treatment with a reducing agent.

4. A monoclonal antibody in accordance with claim 3, produced by a hybridoma selected from the group consisting of hybridoma ATCC HB 10342, hybridoma ATCC HB 10343, and hybridoma ATCC HB 10344.

5. A hybridoma which produces a monoclonal antibody in accordance with claim 1.

6. A hybridoma which produces a monoclonal antibody in accordance with claim 3.

7. A hybridoma selected from the group consisting of hybridoma ATCC HB 10342, hybridoma ATCC HB 10343, and hybridoma ATCC HB 10344.

* * * * *

UNITED STATES PATENT AND TRADEMARK OFFICE
CERTIFICATE OF CORRECTION

PATENT NO. : 5,459,061
DATED : October 17, 1995
INVENTOR(S) : Sato et al.

Page 1 of 2

It is certified that error appears in the above-indentified patent and that said Letters Patent is hereby corrected as shown below:

Column 6, line 14, delete "Ag8," and insert therefor --Ag8.--;

Column 6, line 51, delete "528IGG" and insert therefor --528IgG--;

Column 9, line 61, delete the period after "37°C";

Column 11, line 19, delete "370,000" and insert therefor --37,000--;

Column 11, line 25, delete "170,000" and insert therefor --17,000--;

Column 11, line 41, delete "170,000" and insert therefor --17,000--;

Column 17, line 43, delete "Want" and insert therefor --Wang--;

UNITED STATES PATENT AND TRADEMARK OFFICE
CERTIFICATE OF CORRECTION

PATENT NO. : 5,459,061

DATED : October 17, 1995

INVENTOR(S) : Sato et al.

It is certified that error appears in the above-identified patent and that said Letters Patent is hereby corrected as shown below:

Column 18, line 15, delete "Submitted for publication." and insert therefor --Proc. Natl. Acad. Sci USA 8<u>7</u>: 3151-3155.--

Signed and Sealed this

Eighteenth Day of March, 1997

Attest:

BRUCE LEHMAN

*Attesting Officer*    Commissioner of Patents and Trademarks